(12) United States Patent
Miller et al.

(10) Patent No.: US 9,808,148 B2
(45) Date of Patent: Nov. 7, 2017

(54) SPATIAL 3D STERIOSCOPIC INTRAORAL CAMERA SYSTEM

(71) Applicants: Michael L. Miller, Santa Cruz, CA (US); Walt Froloff, Aptos, CA (US)

(72) Inventors: Michael L. Miller, Santa Cruz, CA (US); Walt Froloff, Aptos, CA (US)

(73) Assignee: Jan Erich Sommers, Santa Cruz, CA (US)

( * ) Notice: Subject to any disclaimer, the term of this patent is extended or adjusted under 35 U.S.C. 154(b) by 236 days.

(21) Appl. No.: 13/830,360

(22) Filed: Mar. 14, 2013

(65) Prior Publication Data
US 2014/0272764 A1    Sep. 18, 2014

(51) Int. Cl.
| | |
|---|---|
| A61B 1/06 | (2006.01) |
| A61B 1/00 | (2006.01) |
| A61B 1/05 | (2006.01) |
| A61B 1/24 | (2006.01) |
| A61B 5/00 | (2006.01) |
| A61B 6/00 | (2006.01) |
| A61B 6/14 | (2006.01) |

(52) U.S. Cl.
CPC .......... *A61B 1/0684* (2013.01); *A61B 1/0002* (2013.01); *A61B 1/00009* (2013.01); *A61B 1/00016* (2013.01); *A61B 1/051* (2013.01); *A61B 1/0638* (2013.01); *A61B 1/24* (2013.01); *A61B 5/0035* (2013.01); *A61B 5/0066* (2013.01); *A61B 5/0088* (2013.01); *A61B 6/14* (2013.01); *A61B 6/5247* (2013.01); *A61B 1/00193* (2013.01); *A61B 2576/00* (2013.01)

(58) Field of Classification Search
CPC ..... A61B 1/24; A61B 1/0684; H04N 13/0296
See application file for complete search history.

(56) References Cited

U.S. PATENT DOCUMENTS

| | | | |
|---|---|---|---|
| 2009/0087050 A1* | 4/2009 | Gandyra | 382/128 |
| 2010/0279248 A1 | 11/2010 | Mourad | |
| 2012/0237890 A1 | 9/2012 | Liang | |

* cited by examiner

*Primary Examiner* — Anner Holder
*Assistant Examiner* — Zhubing Ren
(74) *Attorney, Agent, or Firm* — Walt Froloff

(57) ABSTRACT

Spatial 3D stereoscopic video is generated with a dual camera subassembly in a hand held device. The 3D Left-Right Multiplexed Spatial Stereoscopic video stream is wirelessly coupled to a processing system for simultaneous visualization comparison with intraoral cavity digital dental impression 3D CAD formatted files, Cone Beam Panoramic Computed Tomography images, Optical Coherence Tomography planar images and Panoramic X-ray image digital files for Stereoscopic visualization on stereoscopic displays and occluding viewing glasses.

12 Claims, 14 Drawing Sheets

SPATIAL 3D STERIOSCOPIC INTRAORAL CAMERA SYSTEM

BACKGROUND

Field of the Invention

The present invention generally relates to spatial three-dimensional (3D) intraoral camera system and specifically to intraoral spatial 3D and associated stereoscopic and autostereoscopic display systems.

Intraoral Cameras are used by over 80,000 dental offices in North America alone. They have been instrumental in building patients' trust and confidence through visual communication. While other digital SLR cameras are useful, Intraoral Cameras are used by dental professionals chair side to show the patient a clear picture of the inside of their mouth, allowing the dentist to consult them on various treatment options, and save the images directly to a patient's file for later viewing and comparing, The current intraoral camera is better than the SLR, but still lacking. The ability to discriminate complexity in the intraoral cavity field with the current Intraoral Camera is, a metaphor would be finding a needle in a haystack. A needle would be easier and the needle would be better detected with spatial 3D visualization capability. Complexity discrimination and visual discovery by inspection are the reason stereoscopic 3D displays are incorporated in robotic surgery systems or used with laparoscopic surgery to visualize a macroscopic body cavity. It is easier to navigate and use hand-eye coordination more accurately to promote discovery and effect treatment.

The camera is generally located in the tip of the Intraoral wand and transmits real-time video for dentist and patient to view and review. However, current viewing angles with the Intraoral Cameras are limited to 0 and 90 degrees. While these are better than their predecessor technologies, more is needed. The oral cavity's miniature cave-like geometry with complexity of many teeth obscuring further vision, can easily cause missing an important tiny artifact due to lack of viewing angle or obscured anomaly. Hence mechanisms are need to improve viewing angles and granularity.

Furthermore, the images are displayed on a television or computer monitor, so problems such as worn or broken fillings, cracked teeth, plaque deposits, cavities next to fillings and excessive wear cannot always be discovered by inspection because of visual acuity. Some anomalies remain undetected because the visual acuity was insufficient to see by inspection or display granularity.

What is needed are better dental diagnostics to build patient confidence and further improve dental care as well as anomaly detection in the oral cavity in the course of regular dentist visits.

Dental decay is currently detected through inspection and tactile methods coupled with radiography. These diagnostic and treatment paradigms were developed long ago. Thanks to the introduction of fluoride, the nature of dental decay has changed markedly over the past 50 years, and current methods do not have sufficient sensitivity or specificity for the types of lesions that are typically encountered now. New tools are needed to detect and monitor dental decay, caries, at the early stages of development.

Today's carious lesions are of a more concealed nature: They penetrate deep into the tooth without forming a cavity. Radiographic methods do not have the sensitivity for these types of lesions, particularly occlusal lesions, and by the time the lesions are radiolucent, they often have progressed well into the dentin—at which point surgical intervention is necessary. At that stage in the decay process, it is far too late for preventive and conservative intervention, and a large portion of carious and healthy tissue will need to be removed, often compromising the mechanical integrity of the tooth.

If carious lesions are detected early enough and before cavity formation, it is likely that they can be arrested and remineralized by nonsurgical means. Demineralization causes an increase in the porosity of the tooth, which in turn increases the magnitude of light scattering, and lesions visible on the tooth surface appear whiter than the surrounding sound or normal enamel. During remineralization, the pores near the surface of the lesion are filled with mineral, reducing light scattering. Therefore what is needed are, optical methods for the diagnosis of the current dental maladies.

To make a diagnosis and recommend intervention, it is not sufficient simply to detect a carious lesion or areas of demineralization; it also is necessary to assess the state of the carious lesion and to determine whether it is active and progressing or whether it is arrested and has remineralized. Dental experts believe that optical coherence tomography (OCT) is ideally suited for imaging carious lesions because of the high transparency of enamel in the near-IR, and it is uniquely capable of nondestructive measurement of the internal structure of the lesion. OCT is a non-invasive imaging technique that relies on analyzing the frequency components of backscattered light from the internal structure of an object or tissue. There are off the self systems that use OCT in many non-invasive applications generating either 3-D or real time 2-D imaging with high resolution. What is needed are better OCT advantaged intraoral devices.

Panoramic x-ray is a two-dimensional (2-D) dental x-ray examination that captures the entire mouth in a single image, including the teeth, upper and lower jaws, surrounding structures and tissues. The jaw is a curved structure similar to that of a horse shoe. However, the panoramic x-ray produces a flat image of the curved structure. It is typically set to provide details of the bones and teeth.

A panoramic x-ray is a commonly performed examination by dentists and oral surgeons in everyday practice and is an important diagnostic tool. It covers a wider area than a conventional intraoral x-ray and, as a result, provides valuable information about the nasal area, maxillary sinuses, tooth positioning and gum and bone irregularities. Unlike a traditional intraoral x-ray where the film is placed inside of the mouth, the film for a panoramic x-ray is contained inside of the machine. Today, most images are digital files that are stored electronically. These stored images are easily accessible and are frequently compared to current x-ray images for diagnosis and disease management. What is needed is to make more and better use of these images with spatial 3D.

Cone beam computed tomography (CBCT) is a medical imaging technique consisting of x-ray computed tomography where the X-rays are divergent, forming a cone. CBCT scanners are now finding many uses in dentistry. During a CBCT scan, the scanner rotates around the patient's head, obtaining up to nearly 600 distinct images. The scanning software collects the data and reconstructs it, producing what is termed a digital volume composed of three dimensional voxels of anatomical data that can then be manipulated and visualized with specialized software.

As a 3D rendition, CBCT offers an undistorted view of the dentition that can be used to accurately visualize both erupted and non-erupted teeth, tooth root orientation and anomalous structures that conventional 2D radiography cannot. What is needed is to bring some texture and depth into the current CBCT 3D.

Another technology, Digital impression taking uses devices to develop an accurate replica of the teeth being impressioned. Several promising new digital impressioning apparatuses have entered the market in the past few years. Digital impression-taking devices output CAD 3D formatted files. An object of the invention is to harness these planer 3D technologies and integrate them into the spatial 3D world.

VRML, Virtual Reality Modeling Language, is a standard file format for representing 3-dimensional (3D) interactive vector graphics. It has been superseded by X3D standard, but still is very much in use. Many 3D modeling programs can save objects and scenes in VRML format. VRML files are commonly called "worlds" and have the *.WRL extension. Digital impression CAD 3D formatted files, CBCT 3D images, and panoramic x-ray images are commonly stored in .WRL file format. Another object of the invention is to read the .WRL formatted files from current planer 3D and convert those to spatial 3D format for viewing alongside with the invention realtime intraoral spatial 3D viewing.

SUMMARY

The present invention discloses a system and method for a spatial 3D stereoscopic intraoral camera system. The device is a high tech invention containing all of the electronic components such as processor, memory, wireless chips, frame grabber and processing logic for capturing duel CCD images from dual side-by-side camera CCD subassemblies. The sensor subassemblies each having an optical path through a lens disposed to direct light to a CCD, each lens comprising an optical path through an optical lens or pin hole disposed to direct light on CCD, the duel side-by-side subassemblies each having a CCD imaging chip converging optical paths of subassemblies by tilt, tilt range of between 89° to 85° off normal, or shifted subassemblies with shift gap of between 0.5 mm and 5.0 mm, for focus control to achieve the stereoscopic convergence. The CCDs are operatively connected and mounted on daughterboard's with a lens focal gap of between 0.01 and 3.0 mm each. Each subassembly is surrounded by an array of LEDs. Each subassembly is surface mounted on a motherboard supporting electronic components for processing the daughterboard signals and LEDs, motherboard or card software instructions in the form of device logic stored in memory for enabling the device, under control of the processors to format the signal images for wireless transport to remote processing for storage and rendering in 3D Line Sequential Left-Right Multiplexed Spatial Stereoscopic format. The spatial 3D intraoral images are converged and captured by the duel subassemblies for processing and display in stereoscopic presentation and viewing.

The spatial 3D stereoscopic intraoral camera system has an LED array comprising high-efficiency very bright white light, LED's interspersed between an RGB based LEDs that can be tuned to a specific color temperature. Interspersed with discrete blue 400 nm to 450 nm wavelength UV illumination so as to illuminate in UV, tunable white and up to near infrared light spectrum.

BRIEF DESCRIPTION OF DRAWINGS

Specific embodiments of the invention will be described in detail with reference to the following figures.

DETAILED DESCRIPTION

Figure 1:
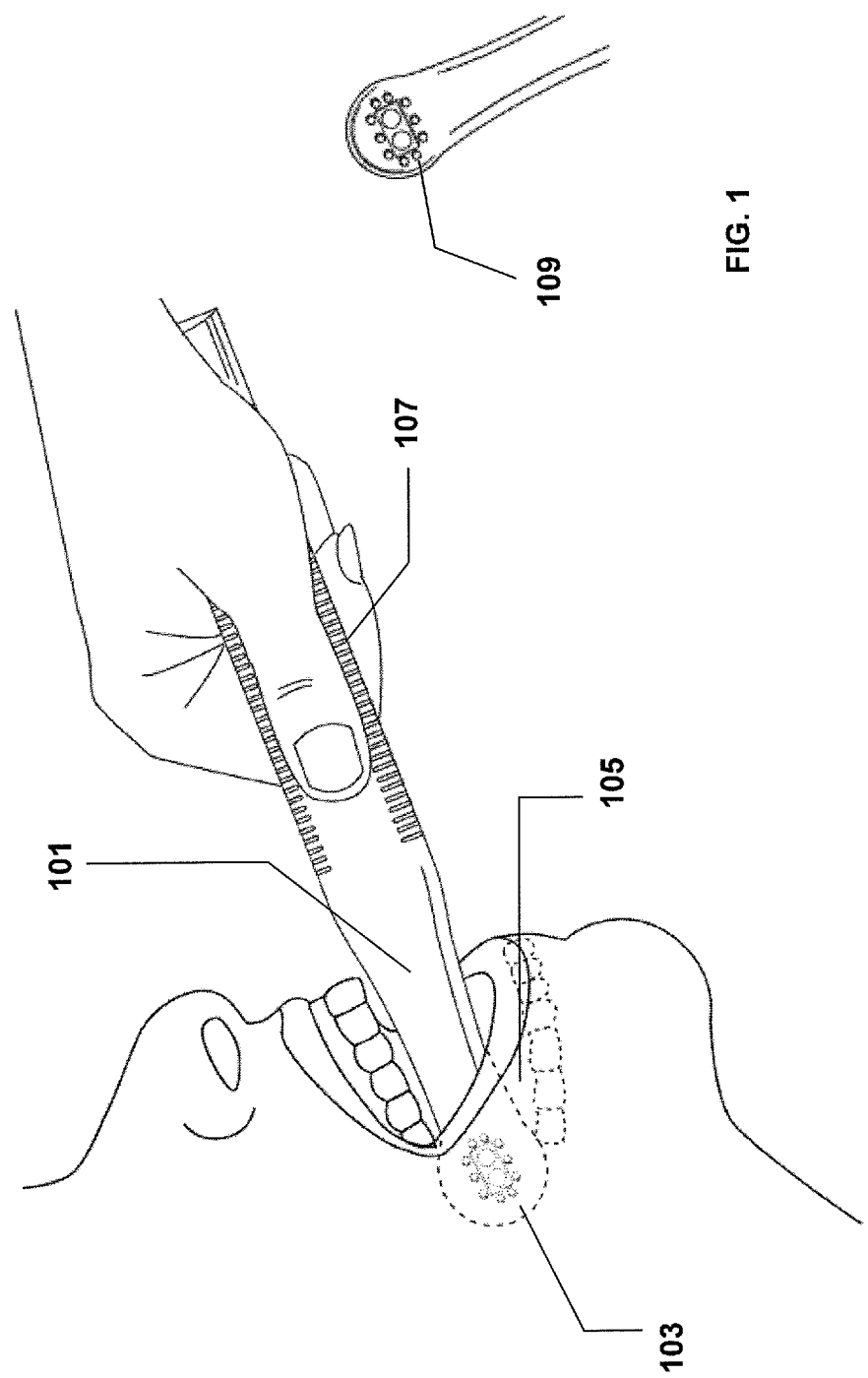
FIG. 1 illustrates the basic intraoral spatial 3D camera system in accordance with an embodiment of the invention.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Objects and Advantages

The present invention discloses a 3D intra-oral camera system with a high resolution 3D spatial stereoscopic viewer for inspecting the interior cavity of the mouth, thereby providing dental practitioners with previously unparalleled depth of field and visual accuracy unreachable with existing methods.

An object of the invention is to allow dentists and oral surgeons to more precisely detect and discern tooth and gum related problem issues including high impact diseases, such as oral cancer and make it less likely that they will escape detection thereby possibly saving lives.

It is another object of the invention to construct a system that would operate to give a more functionally useful visualization to augment dental exams, therapy and repairs. Therefore the 3D spatial intra-oral handheld camera incorporates two side-by-side camera Charge Coupled Device (CCD) sensor assemblies and interfaces with the 3D display unit with a wireless interface or an USB cable.

The spatial 3D visualization will allow the dentist to more accurately conduct an examination and instill patient confidence while they both view the 3D visualization on the 3D spatial stereoscopic display.

It is yet another object of the invention to enhance the patient's ability to recognize problems with the dentist. The spatial 3D visualization allows the dentist, the ability to more accurately detect the orientation of teeth and assess their condition in the oral cavity. The intra-oral camera visualization would enhance patient confidence in any examination and procedure. Patients would clearly see problems being identified by the dentist and their position in the oral cavity.

It is another objective of the invention to combine the Intra-Oral laser scanner dental impression system handheld unit and the Intra-Oral 3D camera handheld unit in a single handheld unit.

Accordingly, it is an object of the present invention to provide a system for complete and comprehensive 3D spatial intraoral exams, including but not limited to:

A complete cavity check, performed tooth by tooth, and recorded in a detailed tooth chart. The conditions of the teeth and mouth are automatically documented in video record. Specifically, digital records are kept about: existing work done on the teeth, decay, leakage, treatments which need to be done, positions of teeth and impactions. The Dentist will check fracture lines, old fillings, broken teeth, identify congenitally missing teeth, and look for deformed teeth, or teeth with abnormal wear, which may or may not be caused by drifting teeth illuminated by the spatial 3D visualization. Another component of the invention enables a diagnosis of a Hard Tissue Intraoral Exam includes checking for abnormal jaw bone growth.

The Hard Tissue Intraoral Exam is followed by a 3D spatial Soft Tissue Intraoral Exam to maintain a more complete profile of a dental history. The 3D intra-oral soft tissue examination includes checking the soft tissues of the mouth, the throat, the tongue and the gums. The 3D intraoral Soft Tissue Intraoral exam begins with an examination of the lips and the mucosa inside the lips called the labial mucosa. The labial mucosa will be examined by gently turning the lip out. The labial mucosa should appear wet and shiny.

The 3D intra-oral examination proceeds to the inside of the cheeks, called the buccal mucosa. Two mirrors will be used in a thorough and stepwise process, moving from one side of the mouth to the other. The hard palate is the firm area of the roof of the mouth, the soft palate is the soft area behind the hard palate. The Dentist will examine both areas visually, and shine a light in the throat, to look for anomalies that are enhanced by the 3D spatial visualization. The top of the tongue will be examined first, followed by the sides of the tongue. The tip of the tongue will be held with a piece of soft gauze and the tongue will be moved gently from one side to the other. The Dentist is looking for swelling or palpated areas, and possibly ulcers. The tissue in this area should be soft. The underside of the tongue will also be examined. Particular attention is paid to the sides of the tongue and the floor of the mouth, as cancers develop in these areas more frequently than on the top of the tongue or the palate. Oral cancers may have the appearance of ulcers, masses, red areas, or white areas. Now the clinician will examine the floor of the mouth.

Finally, the clinician will examine the gums, which are called the gingiva. Healthy gingiva is pink, and regular. Some abnormalities include generalized or localized swelling, redness, ulceration or bleeding. An oral cavity under 3D spatial UV illumination displays what may be abnormal. The attached gingiva and anterior tonsillar pillars, for example, often have a naturally darker appearance. Pigmented tissue appearing dark under white light usually also looks dark under 3D UV illumination. Inflammation typically appears darker under 3D UV illumination due to the excess blood content.

Through the 3D spatial UV illumination, the dentist can discover the suspicious, typically darker, areas. While applying a light amount of pressure with the back side of an explorer or similar instrument in a sweeping motion to diffuse any blood from the area. If the normal green fluorescence returns with this pressure, then the lesion may have an inflammatory component. Inflammation, the buccal mucosa, lateral surfaces of the tongue and hard palate may sometimes show darker areas typically characterized by poorly-defined borders. Hyperkeratosis may often appear bright under 3D UV illumination because of strong keratin fluorescence. Characteristics that Increase Suspicion of Dysplasia and/or Oral Cancer.

Yet another object of the invention is to provide nondestructive, quantitative method of monitoring demineralization and remineralization in high-risk areas of the tooth, such as the pits and fissures of tooth biting surfaces, through OCT spatial 3D image rendering. This can happen in two ways, by conversion of existing 3D or real time 2D OCT images to spatial 3D formats and rendering on stereoscopic displays, or by creating the spatial 3D OCT images from a device.

It is another object of the invention to produce images of carie lesion's highly convoluted internal structure, including the lesion body and surface zone; to aid dentistry professionals in remineralization or repair of existing lesions.

A panoramic x-ray image digital format also allows the dentist to adjust and change the contrast, brightness and darkness of the image for better visualization of certain structures and tissues. Images on film cannot be adjusted or changed. An object of the invention is to convert the digital format to a spatial 3D for viewing along side of realtime oral cavity spatial 3D viewing.

Figures Describing Embodiments of the Invention

FIG. 1 illustrates the basic intraoral spatial 3D camera system in accordance with an embodiment of the invention. The 3D spatial intra-oral handheld camera 107 can have several subsystems including the duel camera head unit 103 incorporating dual camera sensors surrounded by light-emitting-diode (LED) based illumination to reduce shadows. In an embodiment of the invention the LED-based illumination would include high-efficiency very bright white light LED's interspersed between, an RGB based array that can be tuned to a specific color temperature and tunable discrete selectable blue and 400 nm to 450 nm wavelength UV illumination, to illuminate some of the oral cavity 105 dental decay, lesions, lesion depth, occlusion, mineralization, tissue maladies that would be other wise obscured by lesser visibility. The two side-by-side camera CCD sensor subassemblies can be mounted on a motherboard in either a handle axis aligned 103 embodiment or normal 109 to the handle axis 107 in another embodiment.

Figure 2:
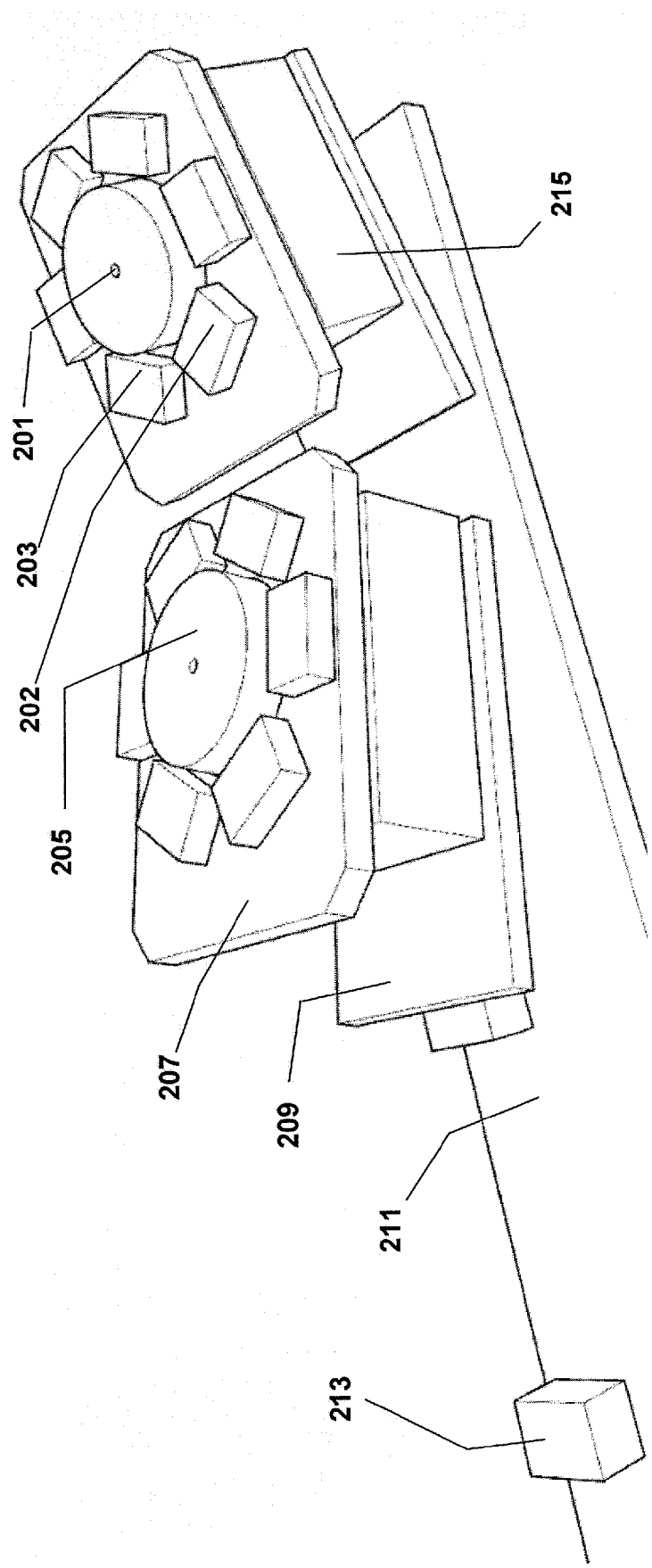
FIG. 2 is a CAD isometric illustration an intraoral spatial 3D camera device heads in accordance with an embodiment of the invention.

FIG. 2 is a CAD isometric illustration an intraoral spatial 3D camera device heads in accordance with an embodiment of the invention. The LED's 203 are symmetrically arranged circling the two camera subassemblies so as to minimize shadows or hot-spots on the target subject. The white light 202 and ultraviolet LED's 203 can be arranged in an alternating pattern or in a sequence three white light, two ultraviolet light, three white light, two ultraviolet light, symmetrically spaced 1 mm apart surrounding the two camera unit subassemblies.

The 3D spatial intra-oral handheld camera unit will incorporate a tunable RGB, by mixing the luminance of red 665 nm green 550 nm blue 470 nm LED's 203 in the array in relationship to each other an aspect of the invention is to produce a unique color temperature for white light illumination also comprising an LED array mixed with a blue LED's that emit light at between 400 nm to 450 nm wavelength. This wavelength excites the dentin which, in reaction, reflects a light signal named fluorescence to differentiate healthy teeth or tissue in addition to daylight illumination selectable full spectrum visualization mode. The circuitry to provide the digital electronics is mounted 213 on the mother board 211.

Figure 3:
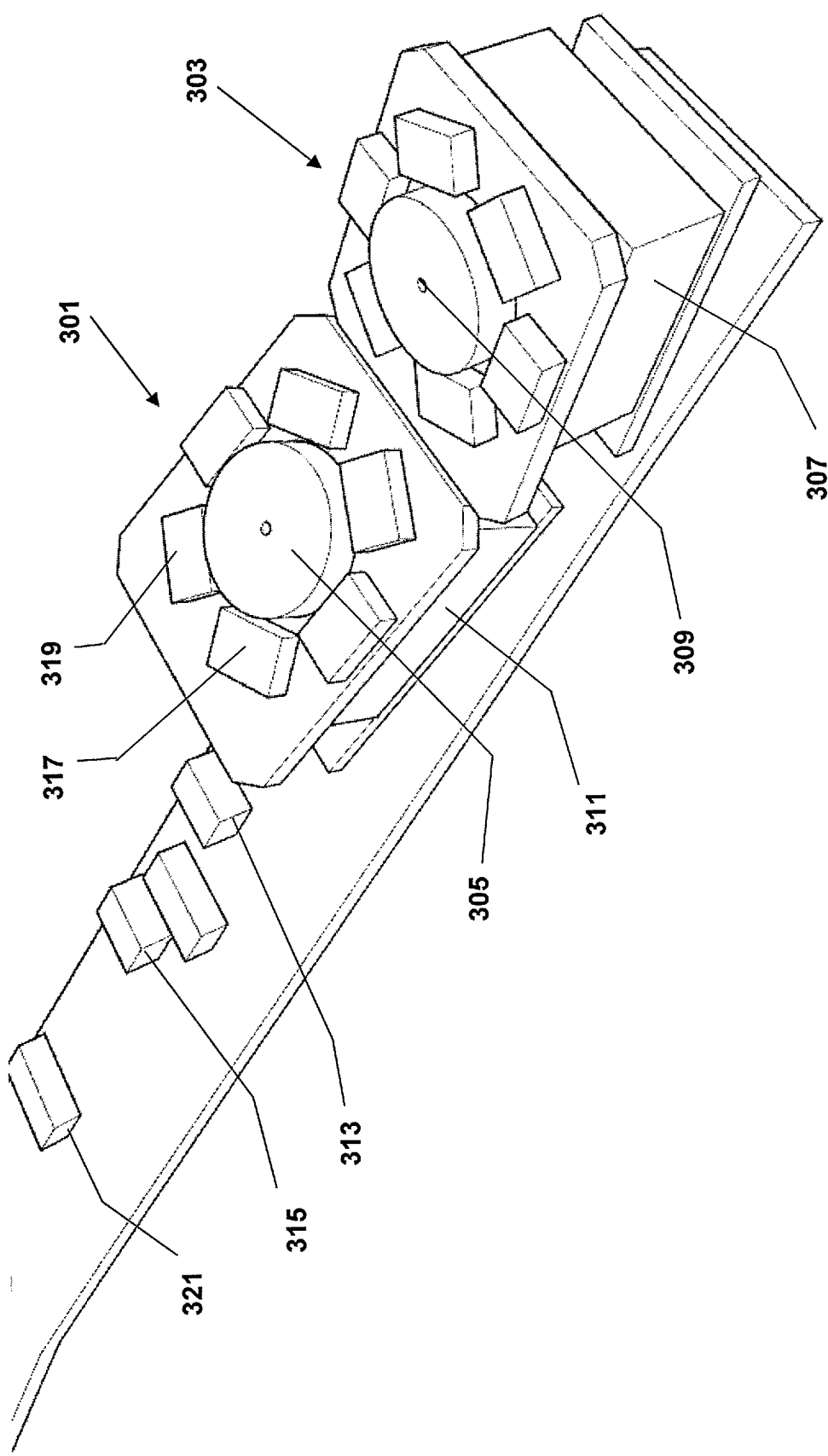
FIG. 3 is a CAD isometric front perspective illustration an intraoral spatial 3D camera device heads on board in accordance with an embodiment of the invention.

FIG. 3 is a CAD isometric front perspective illustration an intraoral spatial 3D camera device heads in accordance with an embodiment of the invention. The duel side-by-side cameras 301 303 can include an optics-based anti-fogging capability, either manually focused, auto-focused or laser machined pinhole lens 305 set for maximum sharpness and infinite depth of field of the 3D spatial visualization of the oral cavity. The stereo pair camera head unit would comprise operatively coupled; stereo pair side-by-side CCD imaging chips camera head 301 303, High resolution camera sensors 305, High-quality optical or precision laser drilled pinhole lens 309, Side-by-side CCD imaging chips are converged by tilt or shift 307 311, for focus control, auto focus or fixed focus, tunable RGB LED switchable array 317 319, dual digital stream raw image frame grabber 313 315, Wireless 2.4 GHz WifI or other wireless video emitter 321, single chip side by side lens's option (not shown), pair of camera head units, side-by-side mount option not shown, and pair of sub assembly camera head units (side-by-side mount—not shown). The imaging chips can be CMOS or other optical capture conversion to digital format devices.

Figure 4:
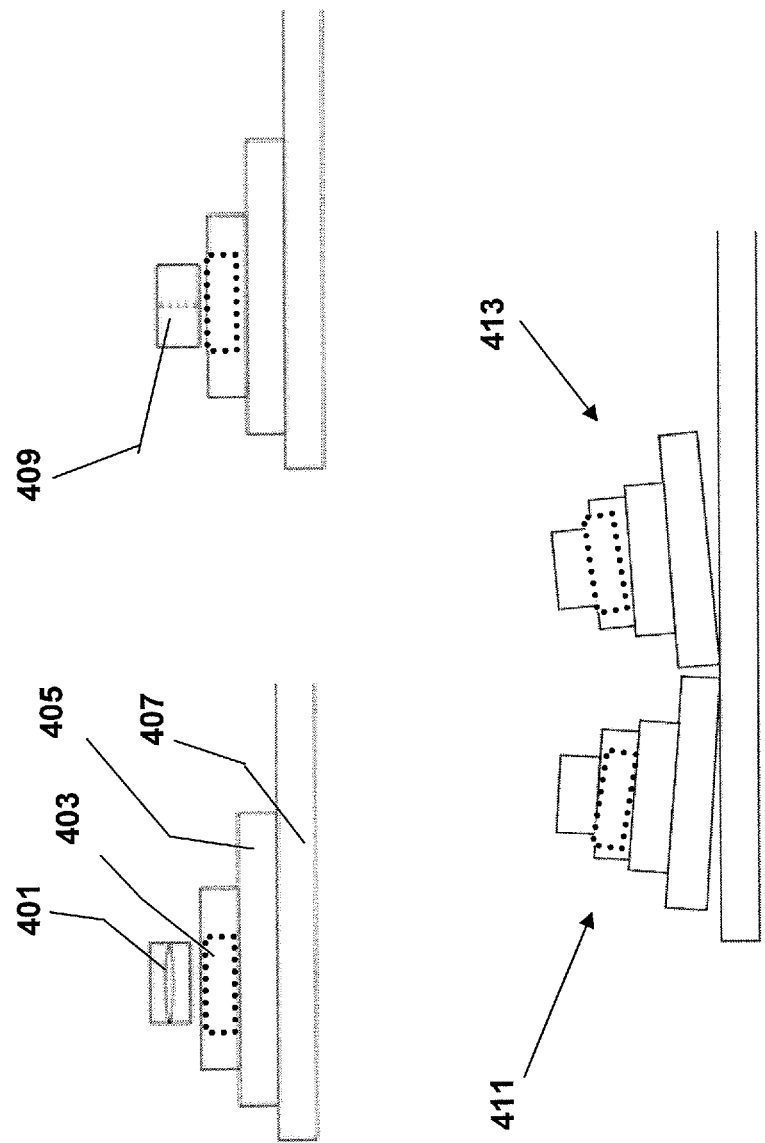
FIG. 4 is a block depiction of lens assembly of an intraoral spatial 3D camera device in accordance with an embodiment of the invention.

FIG. 4 is a block depiction of lens assembly of an intraoral spatial 3D camera device in accordance with an embodiment of the invention. In order to produce the stereoscopic effect a certain amount of optical distortion is necessary for view convergence to 3D. There are at least two optical path methods for the beginnings of optical path, through an optical lens 401 or pin hole 409. The images for the right and left eye would then travel through lens pair impinging the image on their CCDs 403 converting light to signal for further processing on the daughter board 405 surface mounted on the motherboard 407 to a frame grabber and further signal processing downstream. In an embodiment of the invention the lens assembles 411 413 must be tilted with respect to each other on the motherboard, also the component and subassembly mount plane, within acceptable ranges to achieve the stereoscopic convergence using the lens tilt embodiment.

In an embodiment of the invention, the 3D spatial intraoral handheld camera unit can integrate custom optics and a mask to focus two side-by-side lenses 411 413 on a single wide 9×16 CCD imaging chip thereby producing a stereoscopic image in the side-by-side 3D format.

Figure 5:
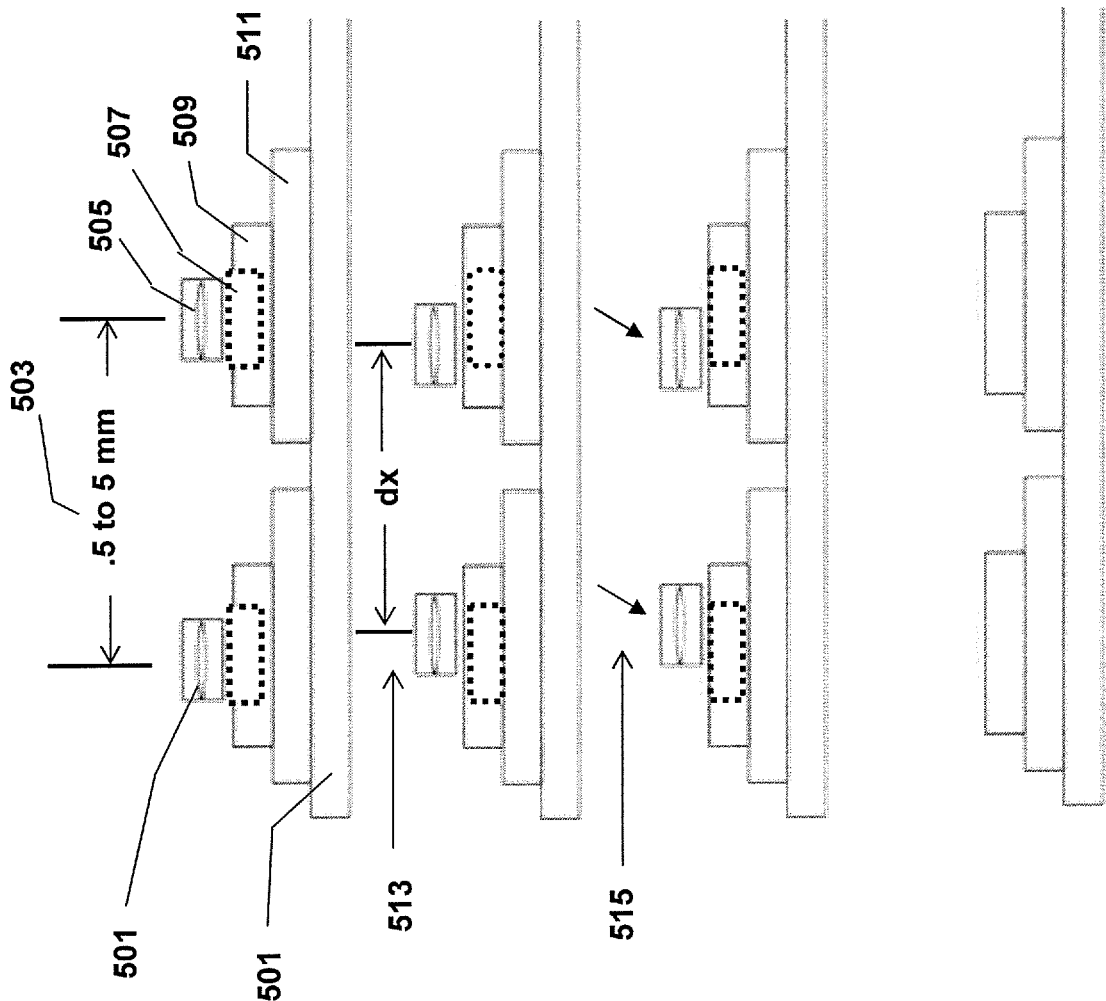
FIG. 5 is a block depiction of device lens shift for image convergence of an intraoral spatial 3D camera device in accordance with an embodiment of the invention.

FIG. 5 is a block diagram depiction of device lens shift for image convergence of an intraoral spatial 3D camera device in accordance with an embodiment of the invention. In an embodiment of the invention, a 3D spatial intraoral handheld camera unit will integrate custom optics and a center 513 to vertical mask to focus two side-by-side lenses 501 503 on a single wide 9×16 aspect CCD imaging chip 507 surface mounted 509 to a daughterboard 511 integrated onto a motherboard 501, also the mount plane, thereby producing a stereoscopic pair of 9×8 aspect raw uncompressed video images in the resulting side-by-side spatial 3D format. Such a 3D spatial intraoral handheld camera unit embodiment can zoom and focus both side by side camera 515 CCD imaging chip 507 optics with shift range dx 513 from 0.5 mm to 5 mm horizontal separation 503 sourced simultaneously with a single control for each respective function mounted on the handle.

Figure 6:
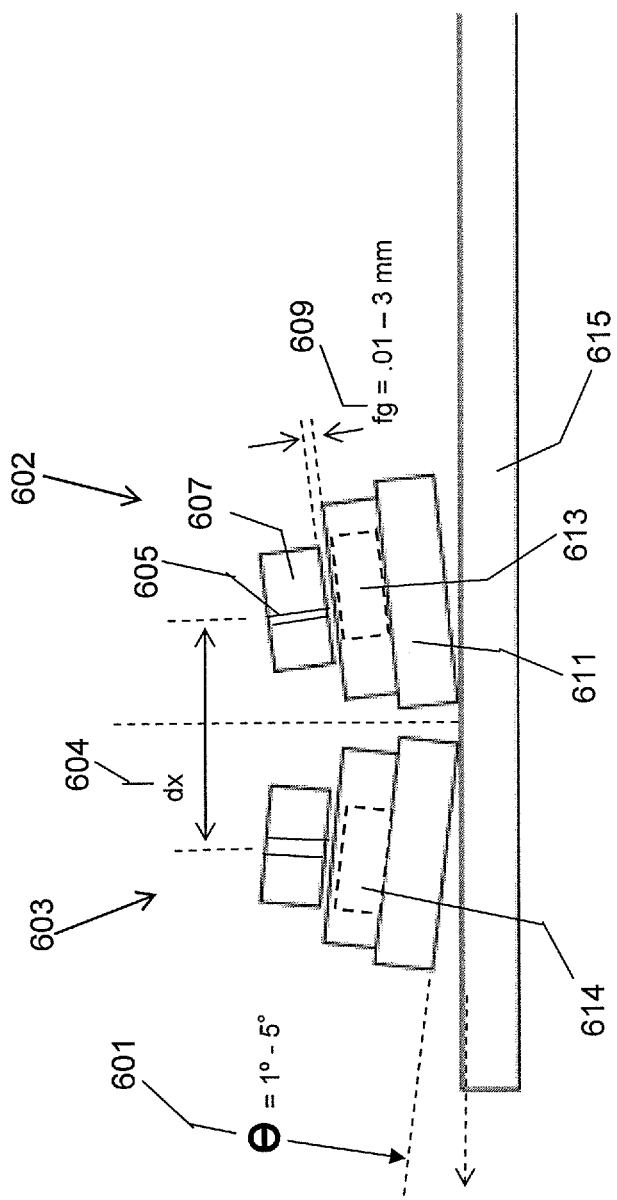
FIG. 6 is a block depiction of device lens tilt for image convergence of an intraoral spatial 3D camera device in accordance with an embodiment of the invention.

FIG. 6 is a block depiction of device lens tilt for image convergence of an intraoral spatial 3D camera device in accordance with an embodiment of the invention.

In a hand held camera lens tilt embodiment, the 3D spatial intra-oral handheld camera unit incorporates two side-by-side CCD imaging chip 613 614 subassemblies 602 603 with a focal length gap 609 of 0.01 to 3 mm, each with their own optical or pinhole 605 lens. Image convergence is controlled by a combination of the tilt angle 601 and the focal gap 609. The two stereoscopic imaging CCD chip subassemblies 602 603 with their respective optical paths 607 are separated horizontally by a shift gap dx 604 of between 0.5 m and 5 mm of separation, symmetric with respect to the duel assembly centerline. The CCD imaging chip 613 subassembly daughterboard 611 can be mounted in the handheld unit parallel to each other along a common horizontal plane mount board 615. The CCD imaging chips 613 and optic subassemblies 602 603 are mounted in the handheld camera unit and are tilted 601 on a vertical plane perpendicular to their horizontal axes and converged on a common subject point. The tilt 601 on an axis in between the two CCD imaging chip 613 614 and optics subassemblies is between 1° and 5° and can be adjustable or fixed to focus the distorted image. A linear slide control or rotating dial control can be used to adjust the relative tilt 601 of between 1° and 5° with the mount plane or motherboard, converging the optical image onto the CCD chip 614 613 and optics subassemblies of the intraoral handheld camera unit embodiment. In another embodiment, the tilt 601 can be made at a fixed angle using a shim mechanism. A linear slide control or rotating dial control on the handle can be used to focus both stereoscopic CCD imaging chip-based optics concurrently or they can be preset at a fixed focus or the CCD imaging chips with a precision drilled pinhole 605 lens 607 which incorporates a focal length from 0 to infinity, for very close quarter oral cavity inspection.

Figure 7:
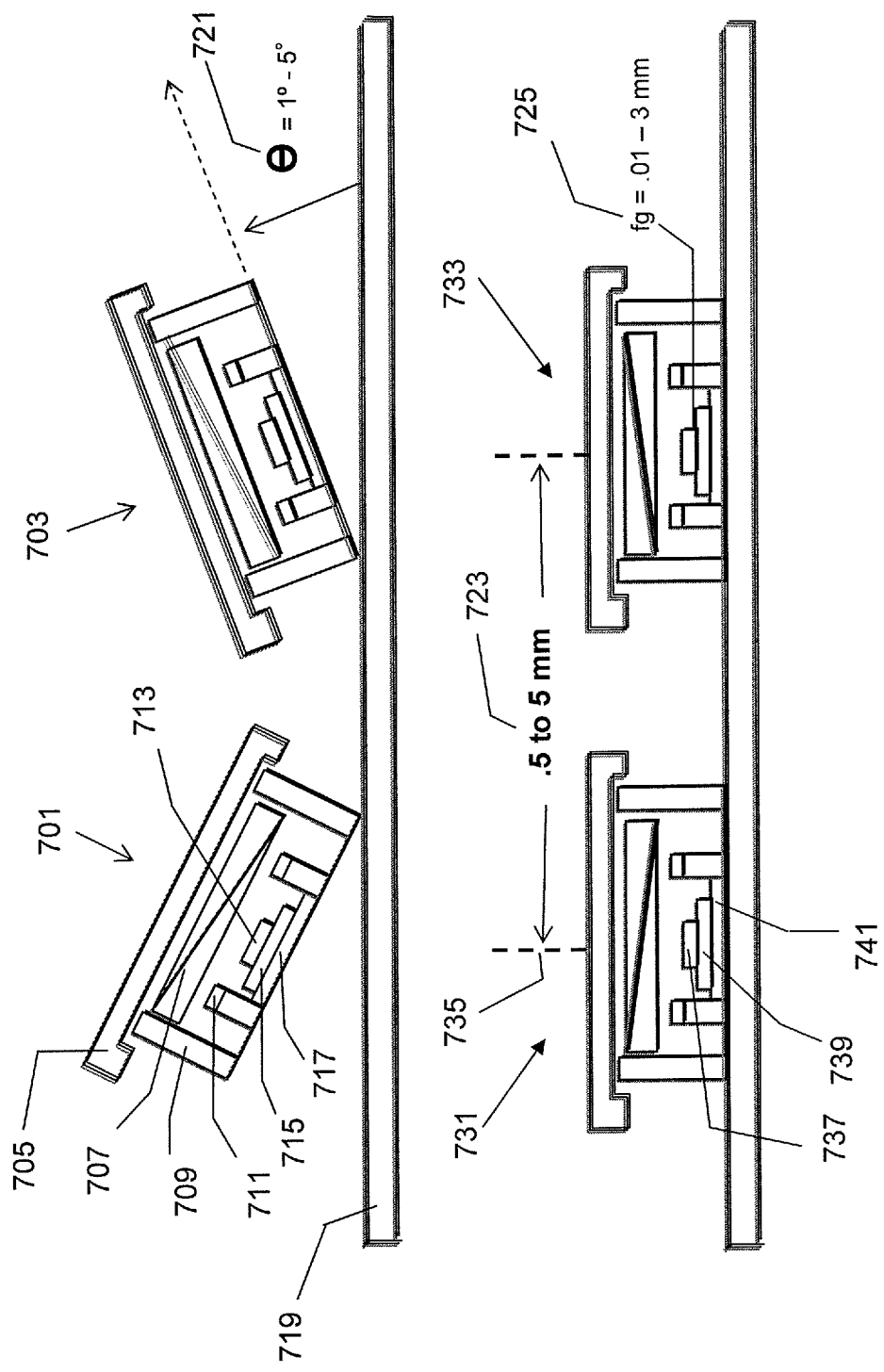
FIG. 7 is a block depiction of device lens tilt and lens shift for OCT image convergence of an intraoral spatial 3D camera device in accordance with an embodiment of the invention.

FIG. 7 is a block depiction of device lens tilt and lens shift for OCT image convergence of an intraoral spatial 3D camera device in accordance with an embodiment of the invention.

In order to produce the stereoscopic spatial 3D display, as with the non OCT technologies, a certain amount of optical distortion is necessary for view convergence to 3D. As with the non-OCT there are at least two duel lens subassembly 701 703 731 733 respectively optical path methods for capturing stereoscopic imaging. The OCT is an interferometric technique, typically using near-infrared light spectrum. The relatively long wavelength superluminescent near-infrared emitting LEDs 711 strategically placed surrounding the lens 713, allows LED EM emitted to penetrate in into the teeth, return and recombine with the interferometric reference optical path.

Near Infrared light is emitted from long wavelength superluminescent near-infrared emitting LEDs 711 through a beam splitter 707. One beam splitter path, the reference beam path, takes the beam to a mirror 709, reflecting back eventually to the lens 713 merging with the oral cavity image reflecting beam at the lens 713. The image beam takes the straight through the beam splitter 707 path and in some embodiments a polarizer 705 lens before reflecting off the oral cavity and back to the lens subassemblies 701 703. The LED 711 emits Near Infrared light, 770-800 nm, from a transparent surface mounted package, and each LED array is situated in a symmetric pattern about each lens 713 737.

The optical lens 713 or pin hole lens focuses the images for the right and left eye which then travel through lens assembly pair 701 703 impinging the images on their subassembly CCDs 715 739 converting light to signal for further processing on the daughter board 717 surface mounted on the motherboard 719, onto to a frame grabber and further signal processing downstream. In an embodiment of the invention the lens assemble pairs 701 702 must be tilted with respect to each other on the motherboard within acceptable ranges of between 1 and 5 degrees 721 from their common surface plan to achieve the stereoscopic convergence using the lens tilt embodiment.

In an embodiment of the invention, the 3D spatial intraoral handheld camera unit can integrate OCT optics and a mask to focus two side-by-side lenses 731 733 on a single wide 9×16 CCD imaging chip or two 9×8 CCD imaging chips thereby producing a stereoscopic image in the side-by-side 3D format. or be shifted 731 733 wrt their centerline between 0.5 and 5 mm 723.

In an embodiment of the invention the polarizer 705, beamsplitter 707 and mirror 709 comprise a snap-on addition to the lens subassembly, allowing the switch between optical OCT and straight visual modes and UV spectrum modes.

The handheld camera unit will integrate custom optics and a center 735 to vertical mask to focus two side-by-side lenses 731 733 on a single wide 9×16 aspect CCD imaging chip 737 surface mounted 509 to a daughterboard 511 integrated onto a motherboard 501, thereby producing a stereoscopic pair of 9×8 aspect raw uncompressed video images in the resulting side-by-side spatial 3D format. Such a 3D spatial intraoral handheld camera unit embodiment can zoom and focus both side by side camera 731 733 CCD imaging chip 737 optics with shift range 723 from 0.5 mm to 5 mm common plan separation sourced simultaneously with a single control for each respective function can be mounted on the handle.

For image convergence in a hand held camera lens tilt embodiment, the 3D spatial intra-oral handheld camera unit incorporates two side-by-side CCD imaging chip 715 subassemblies 701 703 with a focal length gap 725 between the lens 737 and the CCD 739 of 0.01 to 3 mm, each with their own optical or pinhole lens. Image convergence is controlled by a combination of the tilt angle 721 and the focal gap 725. The two stereoscopic imaging CCD chip subassemblies 731 733 with their respective optical paths are separated horizontally by a shift gap 723 of between 0.5 m and 5 mm of separation. The CCD imaging chip 739 subassembly daughterboard 741 can be mounted in the handheld unit parallel to each other along a common horizontal plane mount board 719. The CCD imaging chips 715 739 and optic subassemblies 701 703 are mounted in the handheld camera unit and are tilted 721 on a plane normal to their mount plane so images are converged on a common subject point. The tilt 721 on an axis in between the two CCD imaging chips optics subassemblies 701 703 is between 1° and 5° from the subassembly mount plane and can be adjustable or fixed to focus the distorted image. A linear slide control or rotating dial control on the handheld handle can be used to adjust the relative tilt 721 of between 1° and 5°, converging the optical image onto the CCD chip 717 and optics subassemblies 701 703 of the intraoral handheld camera unit embodiment. In another embodiment, the tilt 721 can be made at a fixed angle using a shim mechanism. A linear slide control 10 or rotating dial control can be used to focus both stereoscopic CCD imaging chip-based optics concurrently or they can be preset at a fixed focus or the CCD imaging chips with a precision drilled pinhole lens 737 which incorporates a focal length 725 from 0 to infinity, for very close quarter oral cavity inspection.

Figure 8:
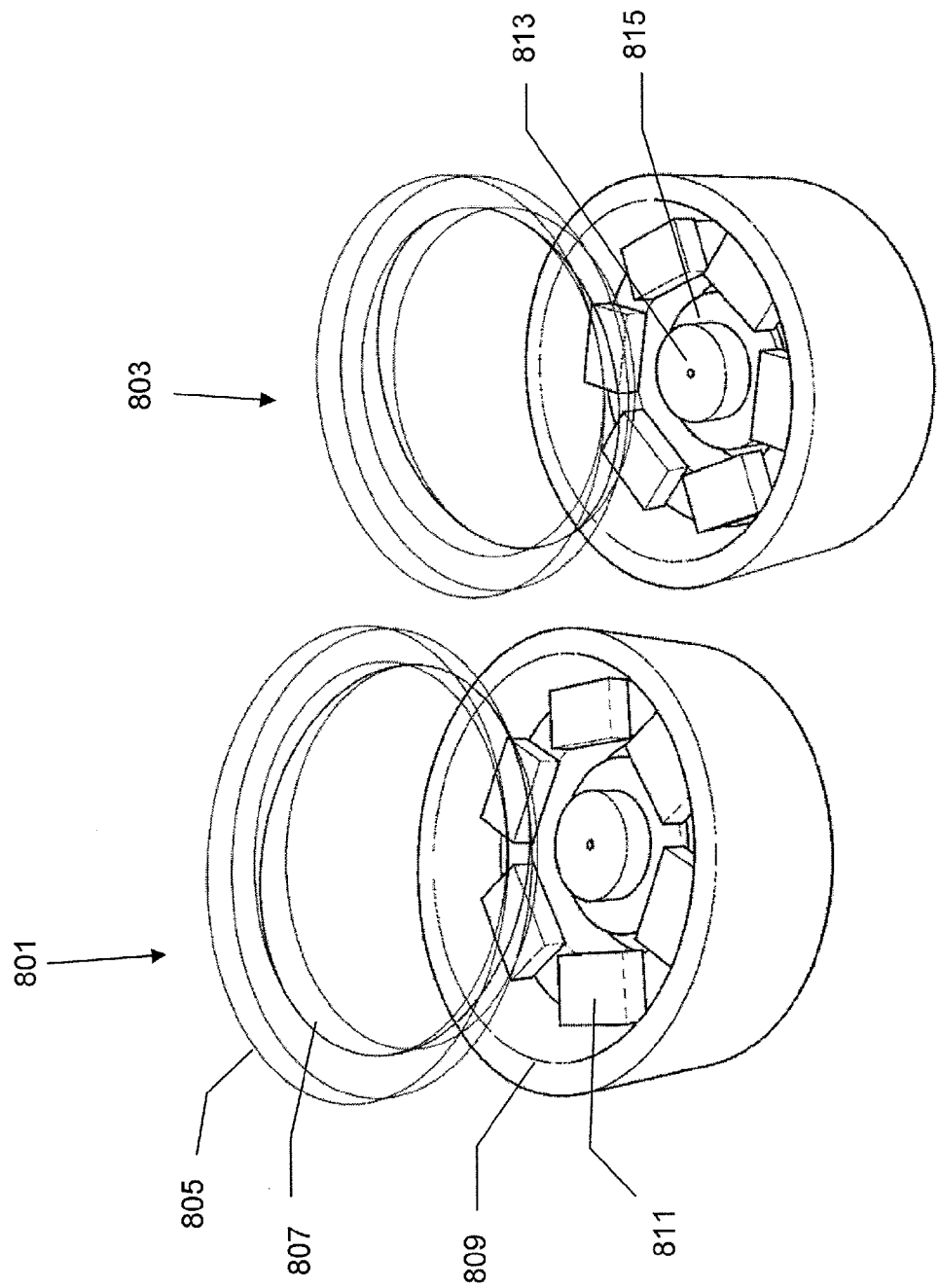
FIG. 8 is an isometric CAD illustration of duel lens subassemblies for OCT spatial 3D camera device in accordance with an embodiment of the invention.

FIG. 8 is an isometric CAD illustration of duel lens subassemblies for OCT spatial 3D camera device in accordance with an embodiment of the invention. The duel cameral subassemblies 801 803 each have a polarizer 805 between a beamsplitter 807 and a lens 813 mounted with a focal gap to a CCD 815. The CCD performs lateral scanning as well as image detection. The beamsplitter 807 splits the emitter LED 811 to a reference path toward the mirror 809 which bounces back into the beamsplitter 807 meeting the image at the beamsplitter headed for the lens 813 for processing. The polarizer 805 lens is positioned orthogonal to the subject to increase contrast.

Figure 9:
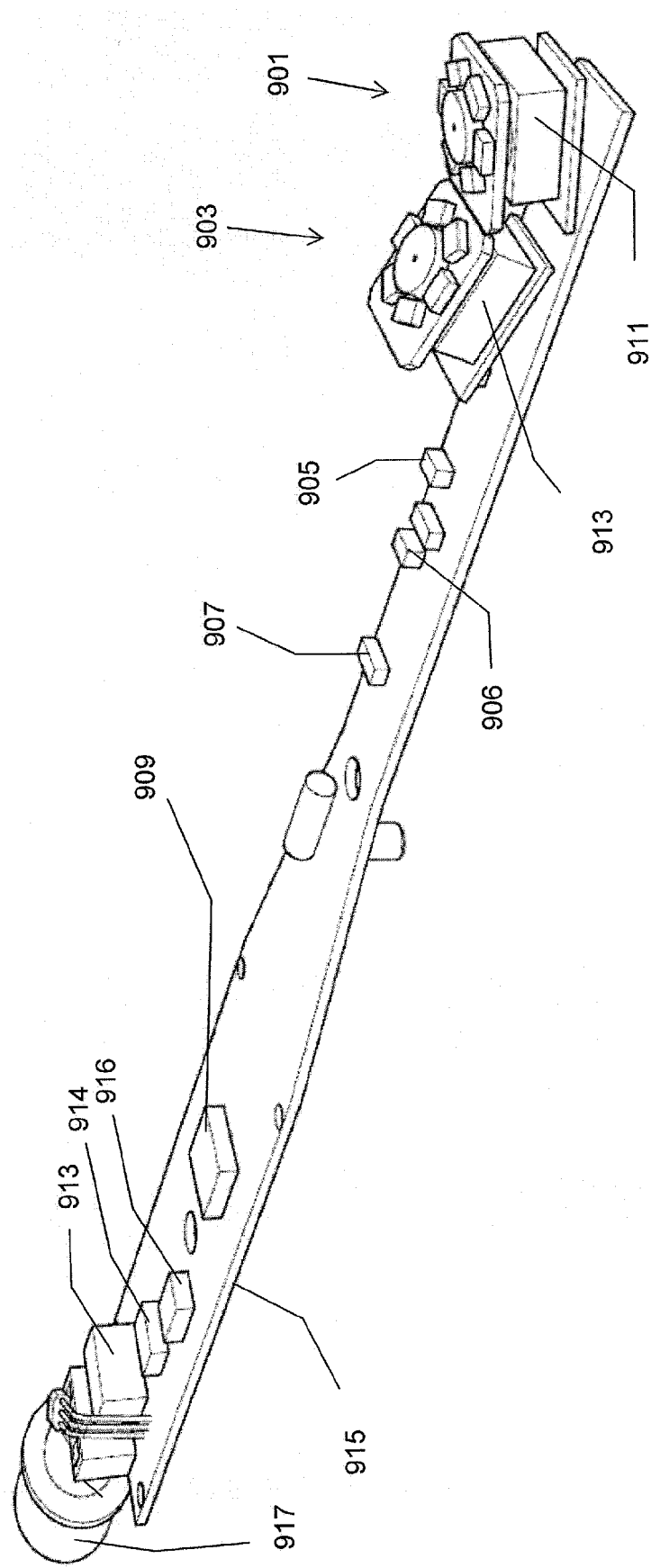
FIG. 9 is a product illustration an intraoral spatial 3D camera device handle with lens horizontal lens head in accordance with an embodiment of the invention.

FIG. 9 is an isometric CAD illustration an intraoral spatial 3D camera device mother board with components in accordance with an embodiment of the invention.

Camera Side-by-Side Motherboard Axis Alignment Orientation

The two side-by-side camera CCD sensor subassemblies 901 903 can be mounted on the handle motherboard 915 in either aligned, as shown, or normal to the board 915 orientation. The handle aligned orientation allows the cameras to maintain a slim profile making it easier to use for visualizing the oral cavity. This orientation also provides an economic position for the dentist to examine an oral cavity where the teeth and soft tissue are aligned in the oral cavity on a horizontal plane. The handle aligned orientation has the benefit of being more comfortable for the dentist to visualize the oral cavity and the 3D spatial viewpoint is orientation sensitive. The handle aligned orientation has an additional benefit of allowing the dentist to more precisely control the position of the spatial viewpoint of the intra-oral camera. The internal circuit 909 PC board 915 built into the handle will incorporate accelerometer 905 that detects the over or under orientation of the handle while being held horizontally so that programming logic can invert the 3D spatial visualization right side up regardless whether or not the dentist is inserting the intra-oral camera unit from the right or left. This will assure the 3D spatial visualization of the intra-oral cavity has the correct orientation from top to bottom consistently and automatically, much like an a mobile display uses to keep the picture level.

Intraoral Camera Handle

The Intra-oral camera handle contains the PC board. The tip of this PC board 915 has the two camera subassemblies 901 903 mounted side-by-side on the handle aligned axes of the PC board 915. The PC board also contains electronic chips 905 and discrete components comprising a frame buffer 905 for accepting images from the CCD chips 911

913, a DSP or processor 906 for containing logic to manage the execution of transfer of images to processing into electronic data 3D spatial formats for wireless transfer downstream, three axis accelerometer 909, electronic multiplexer circuit 907, and a power supply 913 with a controller 916 for the LED's. An LED indicator and switches and controls 914 are mounted on the PC board. The USB supplies 5V DC power 913 to the PC board with a D connector 917 at the end of the handle. A wireless embodiment contains a rechargeable battery and uses standard power technology to re-charge. In another embodiment, 3D spatial intra-oral handheld camera unit can also use a wireless electromagnetic recharging tray system to charge.

In another embodiment of the invention, the handheld unit handle housing encloses an electronic motherboard 915 with electronics and rechargeable battery or USB power supply 913, 3D Camera head with dual high-resolution camera sensors and LED illumination, a Wireless 2.4 GHz, WiFi emitter or other wireless protocol. Light wand, with white or tunable RGB LED to illuminate tissue from behind (what?)

Figure 10:
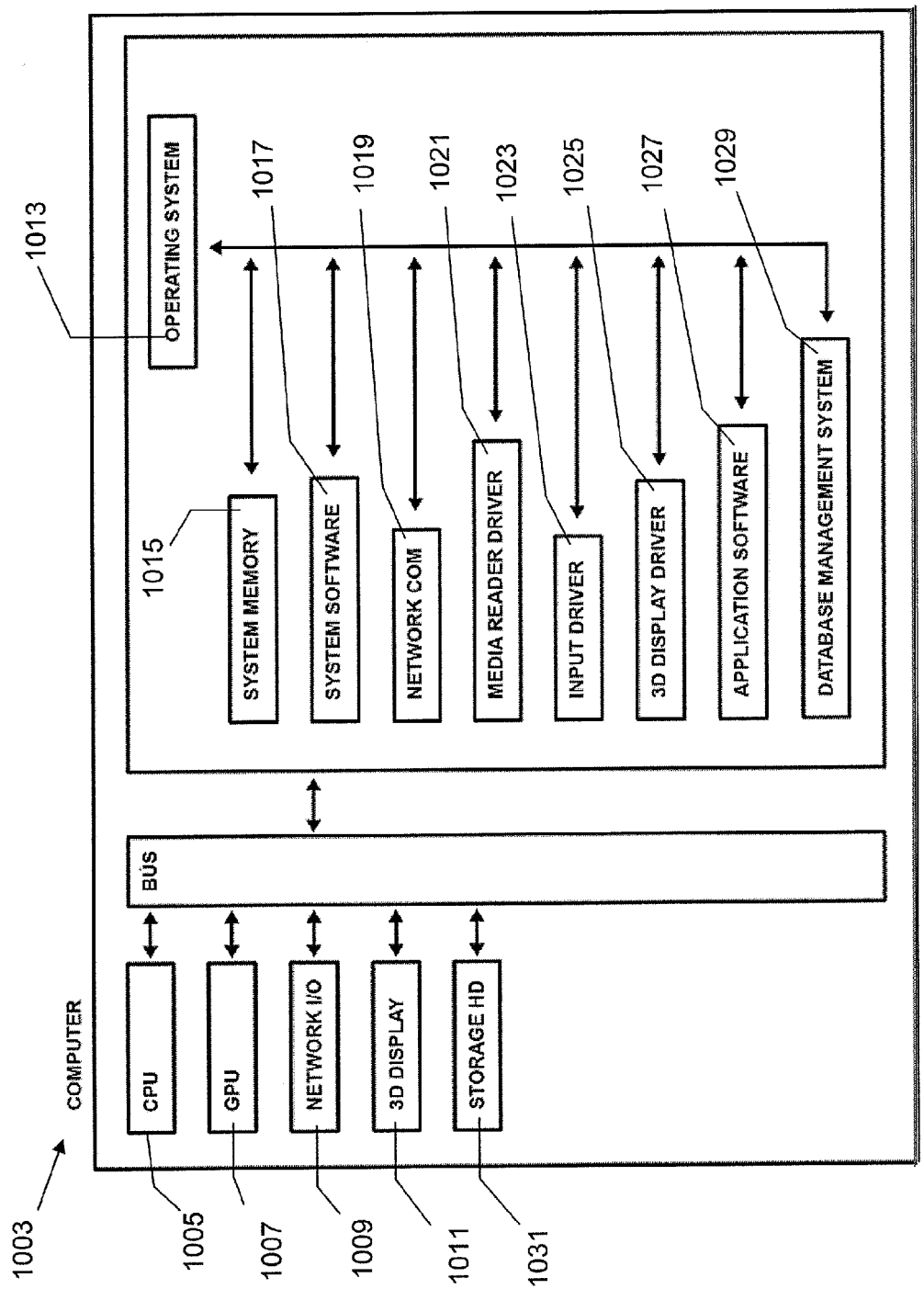
FIG. 10 is a block diagram of the processor system and components for an intraoral spatial 3D camera device in accordance with an embodiment of the invention.

FIG. 10 is a block diagram of the processor system and components for an intraoral spatial 3D camera device in accordance with an embodiment of the invention.

3D Processor System

Planar 3D files from legacy equipment will exist in various formats. An embodiment of the invention will seek these out for display along side with the intraoral spatial handheld device. A computer system 1003 necessary to process the image information comprises a CPU 1005, Network Interface 1009, display device, high speed display device I/F board 1011, Input device I/F, GPU 1007, Media Reader 1021, Memory, Component 1017, Hard drive I/F 1031 and Hard Drive, High performance cooling unit, Wireless or Network I/F 1019, Bundled Software 1017 1027 1029 and OS 1013.

In another embodiment processing and display can be done on a 3D tablet processor with appropriate specifications. These would include a minimum system with a 8.1" High Resolution 1280×800 Touch Screen with Naked Eye 3D, Dual Core Cortex A9, Wi-Fi, Android 4.0.4 or better, 1 GB RAM, 8 GB Internal Memory, 8.1" uncorrected 3D display touch screen (5 point touch), Dual-Core Cortex A9, Mali400 GPU, 0.3 Megapixel front-facing camera, 2.0 Megapixel rear camera, 1 GB Ram, micro SD(HC) Slot, USB 2.0, HDMI output, Gravity acceleration sensor, Wi-Fi, Microphone and USB OTG. With the 3D engine speed chips, 3D image intertwined decoding and a switchable parallax barrier LCD screen to achieve the 3D stereoscopic video without glasses, supportin the popular video formats, 2D Video: MPEG 1/2/4, H.264, MJPEG, VC1, WMV, Real Video format video, up to a maximum of 1080P, Photo Format: BMP, JPG and JPEG, 3D Image: MPO—3D image format, digital cameras support the market MPO—mainstream 3D format JPG, with L/R Interleaving, 3D Video: Left and Right 3D video format, H.264, AVI or other mainstream encoding formats, file name in front of "[3D]."

The Software environment bundle for an embodiment of the invention will include an operating system (OS), 3D custom proprietary display drivers (software safe-area convergence), 3D custom proprietary camera A B player, 3D custom proprietary spatial multiplexed video player, 3D processor graphical user interface (GUI) menu driven control system, dual (2) Universal Serial Bus (USB—2.0-3.0) input line sequential 3D (prototype mux), single USB input stereo pair (USB 2.0-3.0) line sequential 3D, Direct or Open GL CAD visualization line sequential 3D, Web conferencing collaboration line sequential 3D, CAD visualization collaboration line sequential 3D, 3D dental CAD file format converter, 3D stereoscopic raw uncompressed alternating sequential line default format, 3D stereoscopic raw uncompressed over and under switchable format for storage, 3D stereoscopic raw uncompressed side-by-side switchable format for storage, bundled software executable's preinstalled, and 3D dual camera spatial multiplexed wire or wireless channel.

The intraoral camera system hardware-software includes:

A. Processor-Box Unit Embodiment

Compact Windows OS.

Nvidia Quattro GPU board.

Dual video capture or single multiplex 3D video format option.

Wireless 2.4 GHz, Wi-Fi or other wireless protocol.

Software bundle including Web conferencing with 3D content collaboration System applications.

B. 3D Tablet Embodiment 8.1" High Resolution 1280×800 Touch Screen with Naked Eye 3D Dual Core Cortex A9, Wi-Fi, Android 4.0.4, 1 GB RAM, 8 GB Internal Memory 8.1" uncorrected 3D display touch screen (5 point touch), Dual-Core Cortex A9, Mali400 GPU, 0.3 Megapixel front-facing camera, 2.0 Megapixel rear camera, 1 GB Ram, micro SD(HC) Slot, USB 2.0, HDMI output, Gravity acceleration sensor, Wi-Fi, Microphone and USB OTG. With the 3D engine speed chips, 3D image intertwined decoding and a switchable parallax barrier LCD screen to achieve the 3D stereoscopic video without glasses. It supports the popular video formats OV3D app:

The 3D spatial intra-oral handheld camera optionally using a USB 2 or USB 3 to stream the separate right-left camera video signals directly to the main processor system where signals are multiplexed into the selected stereoscopic 3D video display format.

Figure 11:
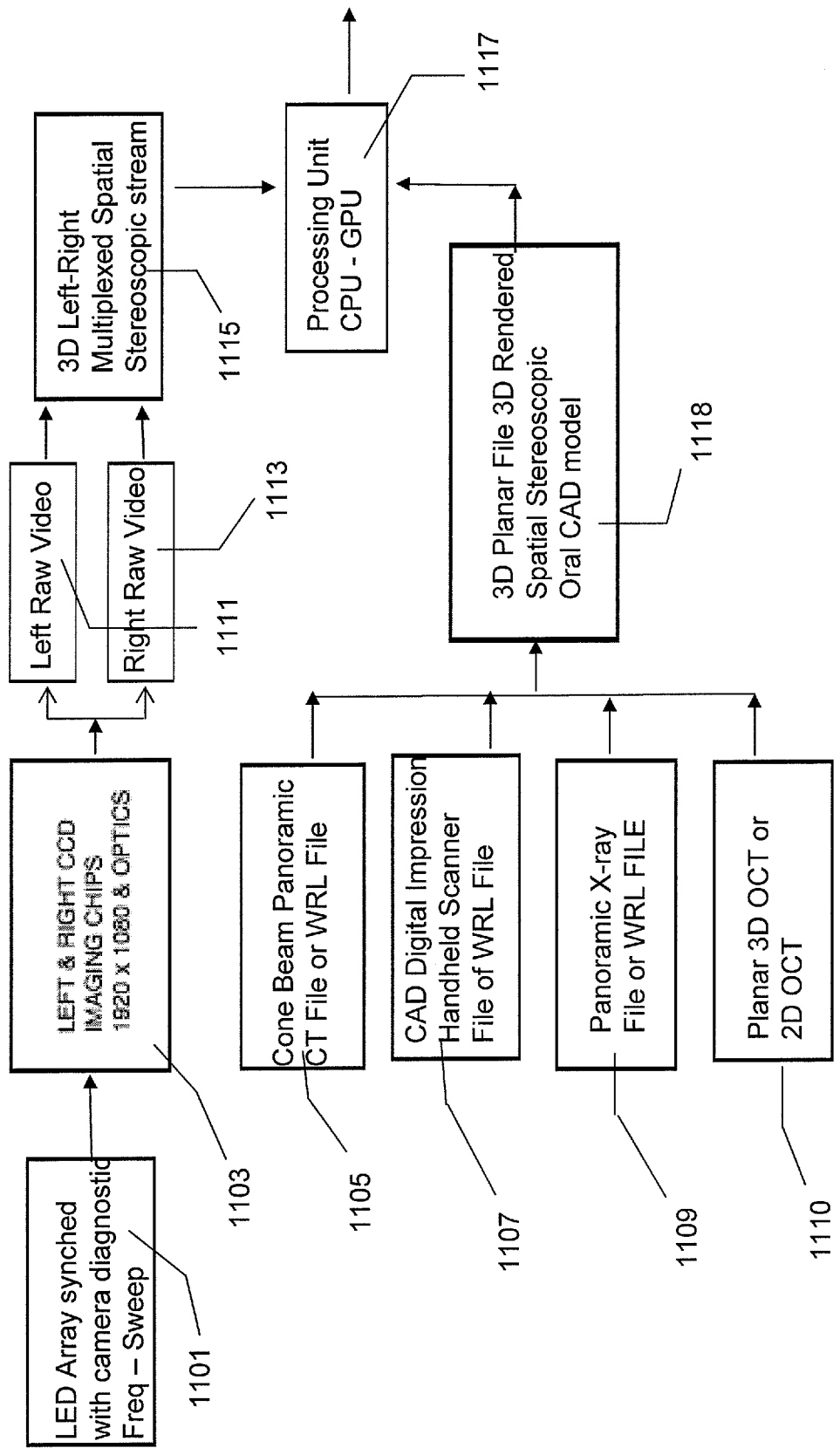
FIG. 11 is a block diagram of the front-end image process flow an intraoral spatial 3D camera device in accordance with an embodiment of the invention.

FIG. 11 is a block diagram of the front-end image process flow for an intraoral spatial 3D camera device in accordance with an embodiment of the invention. Reflected photonics of various frequencies impinging from intraoral camera LEDs will be captured images by the CCDs and converted to image formatted data streams. The camera LED Array photonics in synchronized sweeps selected by user for specific camera diagnostics will generate images in the CCDs from the selected UV, RGB, and near IR frequency spectra 1103. The selected frequency images are captured in the left and right CCD imaging chips 1103 and formatted for the left 1111 and right 1113 video streams to be multiplexed into the 3D Left-Right Multiplexed Spatial Stereoscopic stream 1115. This then raw stream is sent to the processing unit CPU-GPU 1117.

UV blue illumination, from the UV spectrum frequency sweep 1101 stream visually enhances the spatial 3D pattern recognition process for discovering an otherwise difficult to detect oral cancer in early stages. This happens by virtue of the spatial dimension adding real depth and definition to an otherwise planar visual.

An embodiment of the invention will use uncompressed 3D spatial visual files by using raw video streams 1111 1113 and so as not lose visual data from cancerous anomalies and such artifacts through the compression losses. Not easily detectable lesions may prove to be early-stage tissue anomalies such as cancer or gum disease. Thus the LED array of synchronized sweeps with different frequency EM sources 1101 causes the CCD imaging chips 1103 to catch the currently unseen and undetected.

Other technologies currently exist which generate planar 3D images. In an aspect of the invention, these are retrieved and converted to show and compare with the realtime camera in spatial 3D. 3D Planar Cone Beam Panoramic CT File or WRL File 1105, CAD Digital Impression Handheld Scanner file or WRL extension file 1107, Panoramic X-Ray file 1109, and 3D Planar or 2D OCT images where available, are read and rendered 1117 Spatial Stereoscopic Oral CAD model 1118 format. The 3D Spatial Stereoscopic Oral CAD models 1118 are converted and rendered for display with the real-time 3D Left-Right Multiplexed Spatial Stereoscopic stream 1115 by the CPU-GPU and processed for upstream storage, play, playback and display.

Stereoscopic images provide spatial information that is essential in applications like CAD, medical imaging or the like. Stereoscopic imaging is also known as Stereoscopy or 3D Imaging. In an embodiment of the invention, the Cone 1105, CAD 1107, and X-ray 1109 models are scanned from the patient's oral cavity with several different detection devices including a panoramic x-ray scanner or a CT based digital impression system handheld scanner. The respective CAD file formats are converted to 3D spatial CAD formats, the industry standard being spatial stereoscopic format micro-pol. The CAD model images can be used for a proposed dental prosthetic and be pre-visualized with the intraoral camera 3D spatial display system.

3D CAD images are firstly converted to a left and right frame. Then using frame-sequential 3D signal, the left and right frames are sent alternately to the display device and by presentation systems using shuttered glasses or polarized glasses then map the left and right frames to each eye. This involves that the real frame frequency halves the video frame frequency and minimum thresholds must be observed.

In an embodiment of the invention frame-sequential 3D employs frame compatible (CFC) format. This is accomplished by a spatial multiplex that commands the left and right video sequences in one high definition (HD) stream which is coded with H.264 as a single image. This allows streaming video as normal HD video using typical channels and interfaces like HDMI. This method is also compatible with 2D HD mode in the same channel, adding some signaling for switching from 2D to 3D.

The invention can use either of at least two ways to do spatial multiplex: Side by side and Over-Under, but additional proprietary spatial multiplex formats can be used to improve picture quality in other invention embodiments. Side by side format places the left and right images one next to the other in a HD image. In an embodiment of the invention horizontal downsampling through decimation is used. Over-Under format maps left and right images one above the other in a HD image in the stream.

Figure 12:
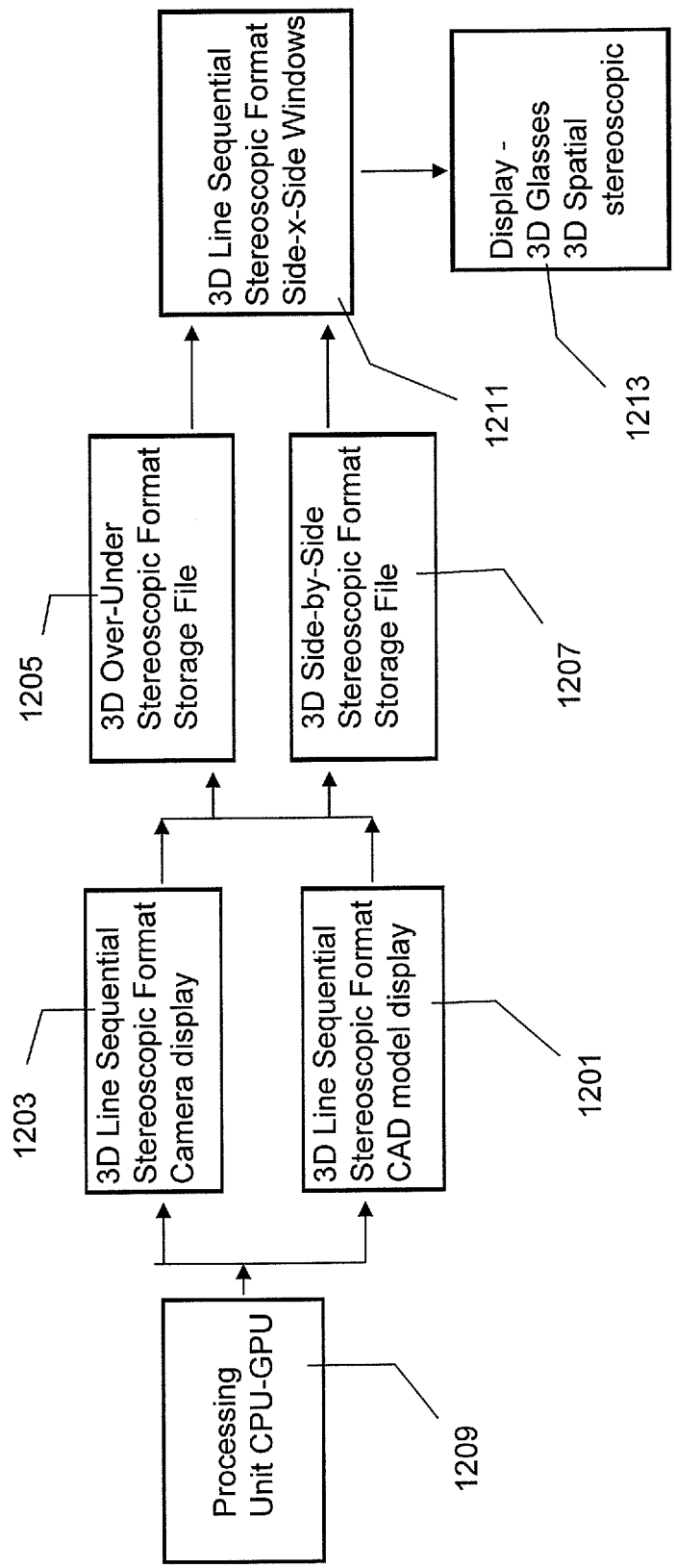
FIG. 12 is a block diagram of the image process flow and display for an intraoral spatial 3D camera device in accordance with an embodiment of the invention.

FIG. 12 is a block diagram of the image process flow and display for an intraoral spatial 3D camera device in accordance with an embodiment of the invention.

The 3D visualization streams from the CPU-GPU 1209 are converted to 3D Line sequential stereoscopic format from the intraoral camera 1203 and the converted CAD model 1201 for display. Each stream 1201 1203 is reformatted to 3D over-under stereoscopic 1205 and 3D side-by-side stereoscopic format 1207 and could be recorded for playback or for recordkeeping storage. In an embodiment of the invention the spatial 3D display system 1211 is used by other diagnostic imaging systems. The processor system 1209 is off-the-shelf parts and standard for video processing.

In furtherance of other legacy systems, another embodiment will by adding a binocular disparity depth cue to the digital images, convert legacy 2D images to 3D and then to spatial 3D format for viewing along side with the intraoral camera spatial 3D system. Optionally, a market 2D intraoral image can be exacted from the raw video data stream to facilitate standard legacy dental recordkeeping and formatted stored files.

Both the handheld intra-oral camera 3D viewpoint video stream 1203 and the spatial 3D visualization rendered from the 3D CAD model 1201 can be recorded in an over and under stereoscopic format 1205 or a side-by-side stereoscopic format 1207 or in the native line sequential format used by the systems 3D display. This would enable the dentist to play back an examination or treatment and become part of the electronic medical record for that patient.

Medical health care is making a large transition in the care and storage of medical files. The dental arena is no different and large video files will need to be recorded and stored for re-use in multiple ways. The intraoral camera 3D visualization data stream would be recorded 1205 1207 for playback or recordkeeping and the 3D display system 1211 could be used for other diagnostic imaging systems in "stripped down" lower dimension formats. In another embodiment a standard 2D intraoral image can optionally be exacted from the raw video data stream to facilitate standard legacy dental recordkeeping equipment. This is accomplished by using a 2D to spatial 3D algorithm to transform the formatted 2D file into spatial 3D. By introducing a binocular disparity depth cue, 2D to stereo 3D conversion and stereo conversion, transforms 2D "flat" film to 3D stereo form, the process of creating imagery for each eye from one 2D image.

The spatial stereoscopic raw uncompressed video content can be formatted in a horizontal sequential line 3D format, a side-by-side 3D format or and over and under 3D format for storage or used by other 3D stereoscopic display systems. All of the 3D content is recorded in raw mode as to not inadvertently compress out any relevant tissue anomalies. The processor system can stream a standard 2D version of any 3D spatial content out to a standard dental practice management computer system concurrently. In another embodiment of the invention, a server can net-conference the 3D intra-oral visualization viewpoint or the 3D spatial visualization of the CAD model to a collaborator in real time.

Figure 13:
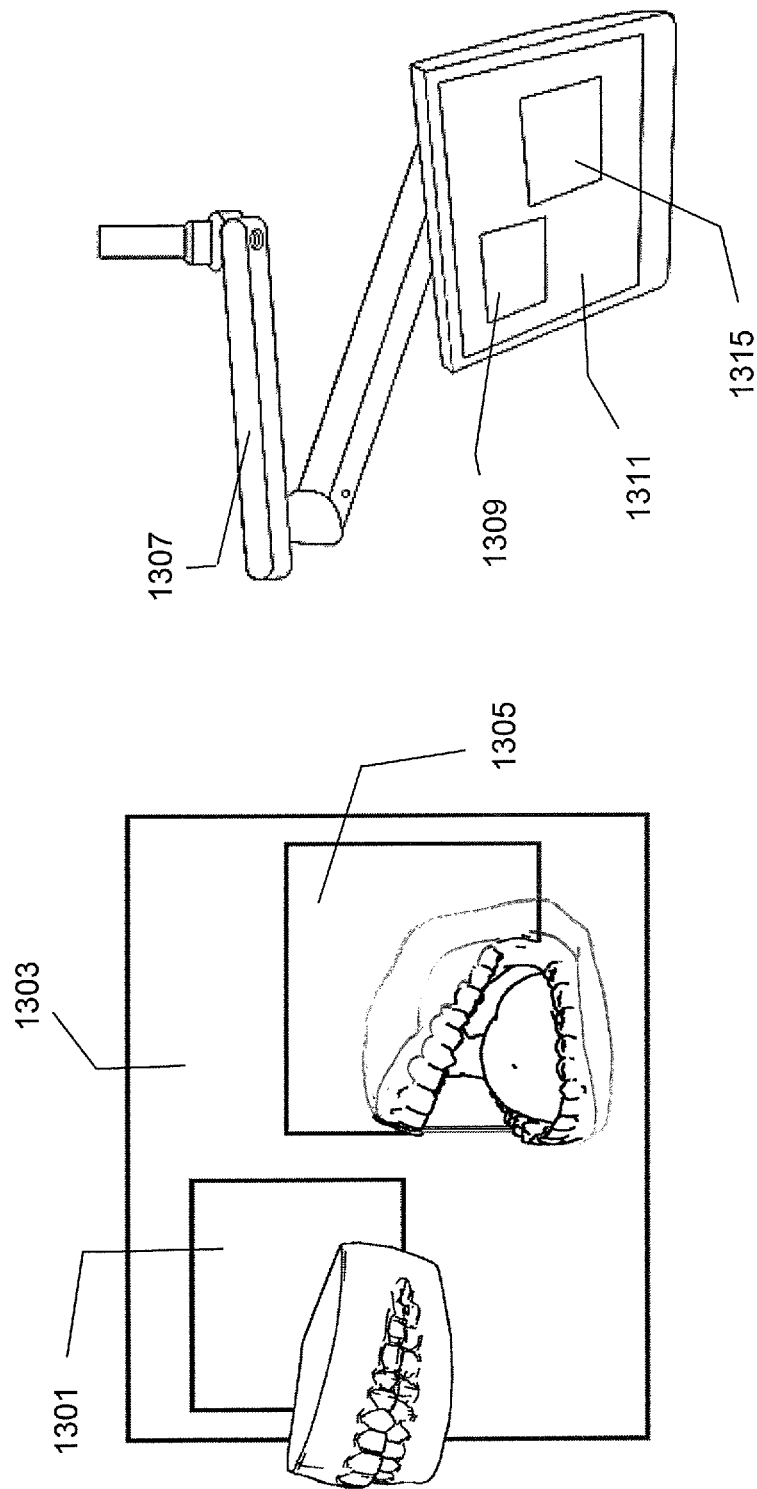
FIG. 13 illustrates CAD 3D and Camera Spatial 3D side-by-side display for an intraoral spatial 3D camera system in accordance with an embodiment of the invention.
Figure 14:
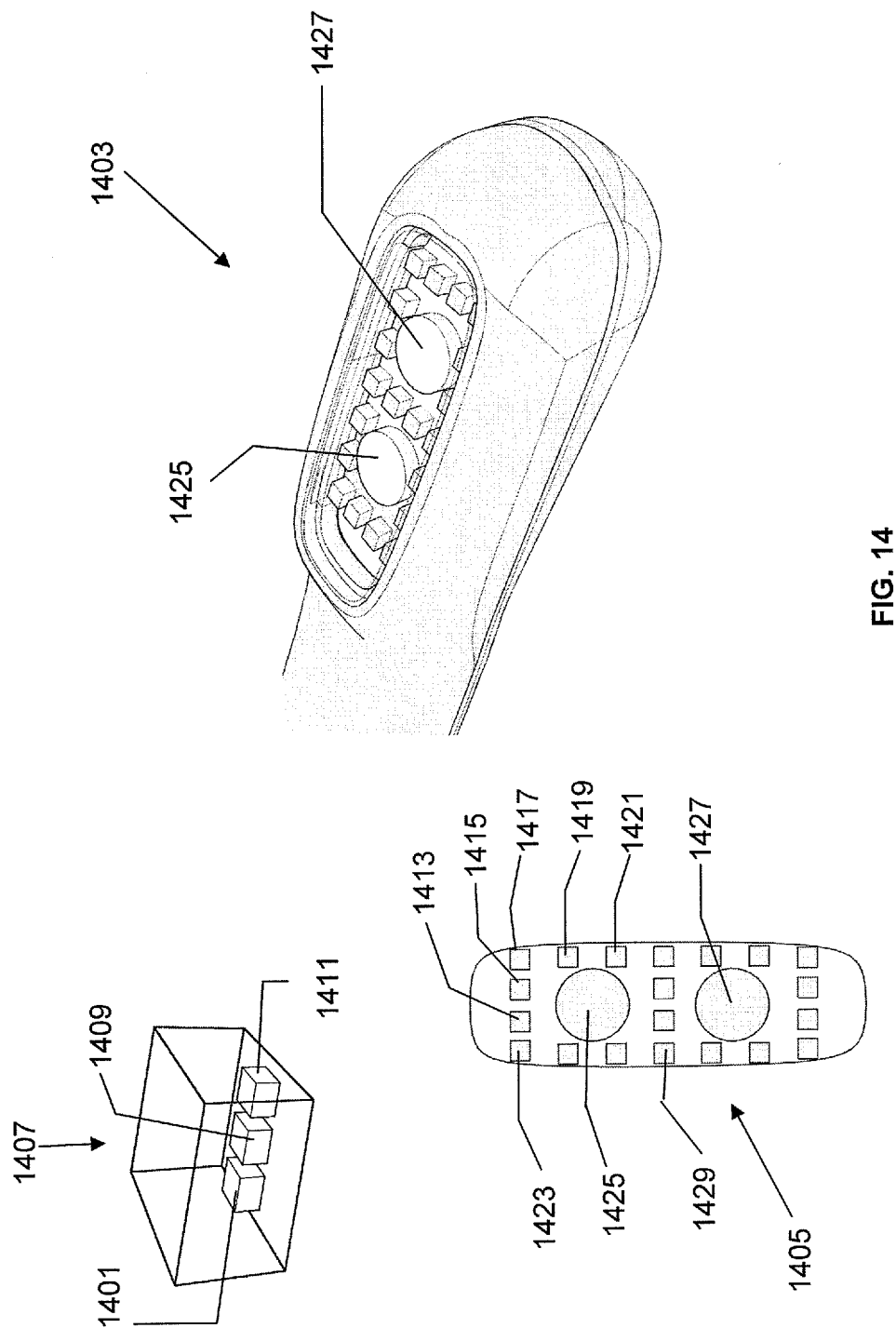
FIG. 14 is a CAD front view illustration an intraoral spatial 3D camera device mother board with components and housing in accordance with an embodiment of the invention.

FIG. 13 illustrates CAD 3D and Camera Spatial 3D side-by-side display for an intraoral spatial 3D camera system in accordance with an embodiment of the invention.

In an embodiment of the invention a 3D stereoscopic display unit 1303 1311 is integrated on an off the shelf articulated arm frame 1307 unit. A PC-based processor system using a 3D GPU accelerator board renders the file input CAD polygonal models in the 3D CAD window 1309 1301 in real time. In addition to displaying the oral cavity in 3D spatial visualization in the intra-oral camera window the processor will render a 3D CAD model of the patient's teeth and lower jaws in another side-by-side window 1305 allowing a dentist to see and compare the real-time intraoral spatial 3D camera 1315 and the spatial rendered CAD 3D 1309 visualizations. The spatial stereoscopic visualization process helps to discriminate visual information and the identification of specific tissue in the pattern recognition process better then a 2D plainer view of the CAD model.

Both the intra-oral camera spatial stereoscopic 3D video stream and the spatial visualization of any CAD models can be recorded for playback or streamed in a collaborative web based net-conference with other dental specialists such as orthodontists and periodontists in real-time. Therefore the 3D spatial stereoscopic streams can be transmitted and observed at remote locations for collaborations.

The additional capability to visualize and compare intraoral dental 3D CAD model in spatial stereoscopic view is enhanced by rendering the model to be manipulated on six axes of orientation with zooming and scaling. Rendering a 3D stereoscopic visualization of a CAD file is like having a virtual model of the oral cavity much like a physical tangible model created from a dental impression out of plastic. By comparing the stereoscopic 3D CAD visualization concurrently with the 3D intra-oral camera real-time spatial visualization of the oral cavity provides the dentist with a new level of comprehensive detail providing a complete examination with unprecedented 3D spatial visual information.

In another embodiment, display is rendered on passive circular polarized safety eye glasses based 3D display system that would yield the highest level of quality for scientific-medical dental visualization. Since some dentists use transparent face shields while conducting examinations or treatments, an embodiment will apply proprietary transparent 3D optical film on the face shield or safety glasses that protect the dentists from spatter's with no discernible interference.

Other embodiments using Off-the-self 3D Stereoscopic Display Systems Fasf3D Display 23" (LG D343P) line sequential film retarder stereoscopic 3D with 3D safety glasses with occluding film based optics.

3D Intra-Oral Camera Live Video Visualization Window and a 3D CAD Dental Model Spatial Visualizer Window (Side by Side Windows) Renders on the Same 3D Display A head-mounted display incorporating 3D spatial stereoscopic twin micro-display elements with optics that allow a user to wear like a pair of glasses the entire display unit. The head-mounted display incorporates a sensor that tracks it's orientation (on the user's head as it moves around as if looking at the virtual image) allowing the dentist to be immersed in a CAD model rendered visualization with a real-time variable head orientation visualization capability. A dentist could also use the head-mounted display to view a spatial 3D visualization from the intra-oral handheld camera unit.

While in a net conferencing mode over a high-bandwidth network the dentists could collaborate with a colleague or specialist while sharing a remote spatial stereoscopic views of the client. 3D visualization from the intra-oral handheld camera unit or be immersed in a CAD model rendered visualization with a real-time look around capability. The real-time visualization of the 3D stereoscopic spatial CAD model could be viewed concurrently in a real-time collaboration with the dental specialist while they can talk to each other and share medical records over a real-time net conferencing online network system with adequate bandwidth.

The system uses a 3D display technology called Film Pattern Retarder (FPR), where a polarizing film coating the 3D display screen allows each eye while viewing with circular Polaroid glasses, to view every other line that incorporates and occludes the right and left pairs of the stereoscopic spatial 3D image rendered by the CAD model visualized from the handheld intra-oral camera unit.

The viewer wears safety eyeglasses which also contain a pair of polarizing filters oriented differently, clockwise/counterclockwise with circular polarization, or at 90 degree angles, usually 45 and 135 degrees, with linear polarization. As each filter passes only that light which is similarly polarized and blocks the light polarized differently, each eye sees a different image. This is used to produce a three-dimensional effect by projecting the same scene into both eyes, but depicted from slightly different perspectives. The use of circular polarizer's is used so that the viewer when tipping his head from side to side will not lose occlusion of the spatial 3D visualization during an examination or treatment.

3D Stereoscopic Imaging is a technique used for creating or enhancing the illusion that an image has depth by showing two slightly offset images separately to each eye of the viewer. Both images are of the same scene or object but from a slightly different angle or perspective. This is meant to trick your brain into synthesizing that the small lateral displacements between the positions of the images are implying spatial depth. Special equipment is usually required in order for the brain to make sense of the picture. The most common applications of stereoscopic 3D need the viewer to be wearing either passive eyewear or polarized glasses.

Stereoscopic Display

In and embodiment of the invention, FPR, Film-type Patterned Retarder is a technology by LG, based on circular polarization and will be used in an embodiment of the invention for spatial stereoscopic display. FPR shows left and right images through different patterns in a circular polarizer. Left/right polarized glasses allow the left and right images to then be seen by the left and right eyes separately. Both images are combined in the brain and generate the 3D effect. FPR 3D shows the both images of left-eye and right-eye simultaneously, dividing the images into right-eye and left-eye by correlation. FPR panels can also be used. FPR improves on the cost of Patterned Retarder (PR) technology that needed to add an extra polarizing glasses substrate to the LCD.

3D Stereoscopic Glasses

Circular polarizer's can be used to create circularly polarized light or alternatively to selectively absorb or pass clockwise and counter-clockwise circularly polarized light. They are used as polarizing filters in photography to reduce oblique reflections from non-metallic surfaces, and are the lenses of the 3D glasses worn for the viewing of stereoscopic movies that use different directions of polarization to differentiate the images to be presented to the left and right eye.

FPR glasses are "passive" and do not use electricity. This means that there is no battery to charge or replace, unlike SG technology. The SG technology can only use glasses which are connected with TV in sync so there are few glasses that viewers can use. In contrast, the FPR technology does not need this process so there is no limit to the amount of people who can watch the 3D display at the same time. In addition, glasses can be shared between different 3D sources, including laptops.

In another embodiment, the display system uses passive circular polaroid safety eye glasses based 3D display system that would yield the highest level of quality for scientific-medical dental visualization. Some dentists use transparent face shields while conducting examinations or treatments. Another example of center integration is are proprietary transparent 3D optical film on the face shield or safety glasses that protect the dentists from spatter's with no discernible interference.

Display Unit 3D alternating horizontal sequential line film retarder 3D micro pol display 23"

3D display in a frame mount with an articulated arm including 3D safety glasses 3D safety glasses or shield with occluding film based optics
LED Array The intraoral cameras duel camera subassemblies sensors are surrounded by LED illumination that is symmetrical to reduce shadows and hotspots. The camera subassemblies include an OCT subassembly 1425 1427 system 1405 1403 illuminated by near infrared LEDs of 770 nm to 800 nm wavelength inside the OCT subassembly 1425 1427 interspersed with high-efficiency super luminance white full-spectrum light LEDs 1413 1415 1419 1421 interspersed further with ultraviolet light LEDs 1423 1421 1417 1429, 400 nm to 450 nm wavelengths. In an embodiment of the invention the LEDs are interspersed in one to two mm segments surrounding the dual camera and OCT subassemblies 1425 1427 in an a pattern incorporating an array of LED packages with each camera subassembly having at least two IR and two UV LEDs 1417 1429 symmetrically positioned about each camera subassembly 1425 1427 and the rest of the LEDs being high-efficiency white light 1413 1415 1419 1421 in a symmetrical pattern surrounding both camera subassembly units.

In an embodiment of the invention, the LEDs in the array each incorporate a tri-state surface mounted LED package 1407. The tri-state LED surface mount plastic package 1407 would include a Red 1401, Green 1409, and a Blue LED 1411 silicon diode unit all mounted in a common plastic light diffusing or translucent plastic package 1407 with a common ground. The LEDs in the light diffusing package can also be a White 1401, White 1409, and a White LED 1411 silicon diode unit.

In another embodiment the LEDs in the array, each incorporate a tri-state surface mounted LED package 1407. The tri-state LED surface mount translucent plastic package 1407 or housing would include a UV 1401, White light 1409, and a IR LED 1411 silicon diode unit all mounted in a common plastic light diffusing plastic package 1407 with a common ground. The tri-state LEDs 1401 1409 1411 could be switched on and off independently or mixed.

The intra-oral camera systems operation would include a full spectrum sweep of the oral cavity starting with an spatial OCT based IR visualization followed by a white light examination, followed by an UV-based examination, followed by an examination illuminated by all of the LEDs mixed together in a sequence. This sequence could be operated by clicking the button mounted on the handle in a continuous four step sequence or programmatically performing the sequence in a timed full spectrum sweep. This type of sequence would allow the camera operator to sweep the oral cavity for problems with both soft and hard tissue problems from the same point of view to compare in a common spatial visualization.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

The invention claimed is:

1. A spatial 3D stereoscopic intraoral camera system comprising:
   processor;
   memory;
   wireless component;
   dual side-by-side camera CCD subassemblies;
   the sensor subassemblies each having an optical path through a lens disposed to direct light to a CCD;
   each lens comprising an optical path through an optical lens or pin hole disposed to direct light on CCD;
   the duel side-by-side subassemblies each having a CCD imaging chip converging optical paths of subassemblies by tilt, tilt range of between 1.degree. to 5.degree. off the surface mount plane, or shift, shift gap symmetrical with the duel assembly centerline of between 0.5 mm and 5.0 mm, for focus control to achieve the stereoscopic convergence;
   the CCDs operatively connected and mounted on daughterboard's with a lens focal gap of between 0.01 and 3.0 mm each;
   each subassembly surrounded by an array of LEDs;
   each subassembly surface mounted on a motherboard supporting electronic components for processing the CCD image signals and LEDs power and control,
   software instructions in the form of device logic stored in memory for enabling the device, under control of the processors to format the signal images for wireless transport to remote processing system for storage and display in 3D Line Sequential Left-Right Multiplexed Spatial Stereoscopic format; and
   each subassembly with programmable logic for frequency sweep through an array of LEDs with source light spectrum spanning from UV to Near Infrared; the LED array source light disposed to enter a beamsplitter in the subassembly adjacent to the lens;
   each beamsplitter refracted incoming light from the LEDs to a reference leg optical path normal to the incoming light and with a mirror on the reference path end reflecting reference beam back to beamsplitter and bending toward the subassembly lens;
   each LED between the beamsplitter mirror and the lens centerline positioned in a symmetric pattern LED array emitting Near Infrared light from a transparent surface mounted LED package and each beamsplitter having a straight through optical path for illumination and reflected image light recombining with reference light on route to the subassembly lens;
   whereby spatial 3D intraoral images are converged and captured by the duel subassemblies for processing and display in stereoscopic rendering and viewing.

2. A spatial 3D stereoscopic intraoral camera system as in claim 1 wherein each LED array comprise high-efficiency very bright white light, LED's interspersed between an RGB based LEDs that can be tuned to a specific color temperature and tunable discrete selectable blue and 400 nm to 450 nm wavelength UV illumination.

3. A spatial 3D stereoscopic intraoral camera system as in claim 1 wherein LEDs are symmetrically arranged encircling each the two camera subassemblies so as to minimize shadows or hot-spots on the target subject.

4. A spatial 3D stereoscopic intraoral camera system as in claim 1 wherein the white light and ultraviolet LED's are arranged in an alternating pattern or in a sequence three white light, two ultraviolet light, three white light, two ultraviolet light, symmetrically spaced 1.0 mm apart surrounding the two camera unit subassemblies, a tunable RGB, by mixing the luminance of red nm green 550 nm blue 470 nm LED's in the array in relationship to each other to produce a unique color temperature for white light illumination also comprising an LED array mixed with a blue LED's that emit light at between 400 nm to 450 nm wavelength.

5. A spatial 3D stereoscopic intraoral camera system as in claim 1 wherein the two side-by-side camera CCD sensor subassemblies can be inline mounted on the internal motherboard aligned either parallel to the board axis or normal to the board axis.

6. A spatial 3D stereoscopic intraoral camera system as in claim 1 further comprising the remote processing system for simultaneous visualization comparison of spatial 3D camera images with the same intraoral cavity in planar 3D CAD digital dental impression files, Cone Beam Panoramic Computed Tomography images, Planar 3D OCT images and Panoramic X-ray image digital files converted into 3D Line Sequential Stereoscopic Format for a side-by-side window spatial stereoscopic rendering.

7. A spatial 3D stereoscopic intraoral camera system as in claim 6 further comprising the capability to visualize and compare intra-oral dental CAD models by rendering the model to be manipulated on six axes of orientation with zooming and scaling for evaluation using the side-by-side complementary visualizations of the same oral cavity from different viewpoints.

8. A spatial 3D stereoscopic intraoral camera system as in claim 1 further comprising the recording, storage and playback of the 3D spatial camera intraoral examination and available intraoral cavity 3D CAD model images converted for spatial 3D stereoscopic viewing.

9. A spatial 3D stereoscopic intraoral camera system as in claim 1 further comprising an accelerometer for over-or-under orientation of the camera device axis while being held horizontally and programming logic to invert 3D spatial visualization right side up regardless of camera device intraoral cavity insertion direction.

10. A spatial 3D stereoscopic intraoral camera system comprising:
    processor;
    memory;
    wireless component;
    dual side-by-side camera sensor CCD subassemblies;
    the sensor subassemblies each having an optical path through a lens disposed to direct light to a CCD embedded in a daughter board;
    the duel side-by-side subassemblies each having a CCD imaging chip converging optical paths of subassemblies by tilt, tilt range of between 1° to 5° off the surface mount plane, or shift, shift gap symmetrical with the duel subassembly centerline of between 0.5 mm and 5.0 mm, for focus control to achieve the stereoscopic convergence;
    the CCDs operatively connected and mounted on daughterboards with a lens focal gap of between 0.01 and 3.0 mm each;
    each subassembly surrounded by a programmable logic for frequency sweep through an array of LEDs with source light spectrum spanning from UV to Near Infrared;
    the LED array source light disposed to enter a beamsplitter in the subassembly adjacent to the lens;
    each beamsplitter refracted incoming light from the LEDs to a reference leg optical path normal to the incoming light and with a mirror on the reference path end reflecting reference beam back to beamsplitter and bending toward the subassembly lens;
    each LED between the beamsplitter mirror and the lens centerline positioned in a symmetric pattern LED array emitting Near Infrared light from a transparent surface mounted LED package;
    each beamsplitter having a straight through optical path for illumination and reflected image light recombining with reference light on route to the subassembly lens;
    each subassembly surface mounted on a motherboard supporting other electronic components for processing the CCD signals and LEDs emissions and
    software instructions in the form of device logic stored in memory for enabling the device, under control of the processors to format the CCD signal images for wireless transport to remote processing system for storage and rendering in 3D Line Sequential Left-Right Multiplexed Spatial Stereoscopic format,
    whereby spatial 3D intraoral images are converged, captured and bundled by the duel subassemblies for processing and display in stereoscopic rendering and viewing.

11. A spatial 3D stereoscopic intraoral camera system as in claim 10 further comprising duel camera subassemblies sensors each surrounded by LED illumination that is symmetrical to reduce shadows and hotspots, the camera OCT subassembly are surrounded outside the OCT mirror wall by interspersed high-efficiency super luminance white full-spectrum light LEDs and ultraviolet light LED array outside of the subassembly mirror wall.

12. A spatial 3D stereoscopic intraoral camera system as in claim 11 further comprising the UV LEDs are interspersed in a symmetric pattern surrounding the OCT subassemblies incorporating an array of LED packages each package having a translucent surface mount package further reducing hotspots and shadows by diffusing the tunable RGB or White Ultraviolet White packages symmetrically positioned about each camera OCT subassembly interspersed with high-efficiency white light LEDs also interspersed symmetric to the each subassembly in the symmetrical pattern surrounding each camera subassembly unit.

* * * * *